United States Patent
Spencer et al.

(10) Patent No.: US 9,606,601 B2
(45) Date of Patent: Mar. 28, 2017

(54) MEDICAL COMMUNICATION HUB AND ASSOCIATED METHODS

(71) Applicant: Volcano Corporation, San Diego, CA (US)

(72) Inventors: Jason Spencer, Rocklin, CA (US); Gerald L. Litzza, Sacramento, CA (US); Craig A. Lindsay, Sacramento, CA (US); Richard Glover, London (GB)

(73) Assignee: Volcano Corporation, San Diego, CA (US)

( * ) Notice: Subject to any disclaimer, the term of this patent is extended or adjusted under 35 U.S.C. 154(b) by 382 days.

(21) Appl. No.: 14/176,892

(22) Filed: Feb. 10, 2014

(65) Prior Publication Data
US 2014/0152467 A1    Jun. 5, 2014

Related U.S. Application Data

(63) Continuation of application No. 14/238,026, filed as application No. PCT/US2012/052241 on Aug. 24, 2012.

(60) Provisional application No. 61/526,990, filed on Aug. 24, 2011.

(51) Int. Cl.
| | |
|---|---|
| *G08C 19/16* | (2006.01) |
| *G06F 1/26* | (2006.01) |
| *A61B 8/00* | (2006.01) |
| *A61B 5/00* | (2006.01) |

(Continued)

(52) U.S. Cl.
CPC .......... *G06F 1/266* (2013.01); *A61B 5/0066* (2013.01); *A61B 5/742* (2013.01); *A61B 8/565* (2013.01); *G06F 13/4081* (2013.01); *G08C 19/00* (2013.01); *G08C 19/16* (2013.01); *A61B 2560/0204* (2013.01)

(58) Field of Classification Search
CPC .......... A61B 2560/0204; A61B 5/0066; A61B 5/742; A61B 8/565; G06F 13/4081; G08C 19/00; G08C 19/16
USPC ..................................... 340/870.02
See application file for complete search history.

(56) References Cited

U.S. PATENT DOCUMENTS

2003/0130590 A1*  7/2003  Bui ................. A61B 5/0002
                                                    600/537
2005/0146431 A1*  7/2005  Hastings ........... A61B 5/002
                                                    340/539.12
2006/0140139 A1   6/2006  DiSilvestro et al.
(Continued)

FOREIGN PATENT DOCUMENTS
WO    WO 2010-150168    12/2010

OTHER PUBLICATIONS

International Searching Authority/Korean Intellectual Property Office, "Notification of Transmittal of the International Search Report and the Written Opinion of the International Searching Authority, or the Declaration," for PCT/US2012/052241, mailed Dec. 27, 2012, 10 pages.

*Primary Examiner* — Omer S Khan

(57) ABSTRACT

A patient communication system having a medical sensing device operable to collect medical data, a network communication module operable to transmit the medical data onto a data network, a controller operable route the first medical sensing data to the network communication module, and a power source operable to provide power to the first medical sensing device, the controller, and the network communication module.

26 Claims, 17 Drawing Sheets

(51) Int. Cl.
*G06F 13/40* (2006.01)
*G08C 19/00* (2006.01)

(56) References Cited

U.S. PATENT DOCUMENTS

| | | | |
|---|---|---|---|
| 2006/0267551 A1 | 11/2006 | Sutardja et al. | |
| 2008/0001735 A1* | 1/2008 | Tran | G06F 19/3418 340/539.22 |
| 2009/0100275 A1* | 4/2009 | Chang | G06F 1/266 713/300 |

* cited by examiner

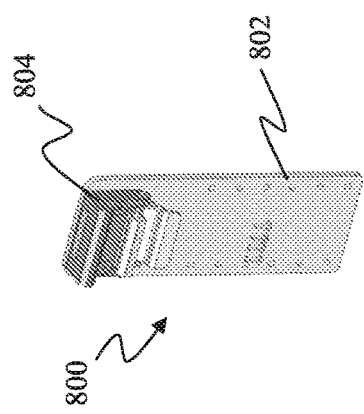
Fig. 8
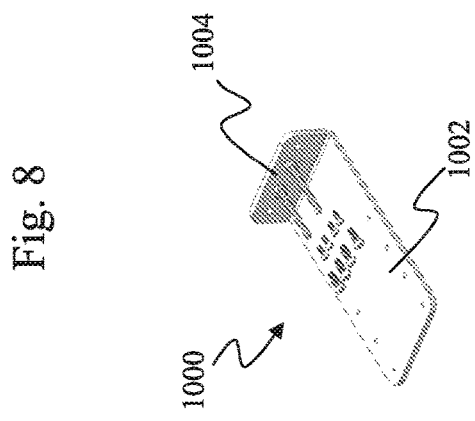
Fig. 10
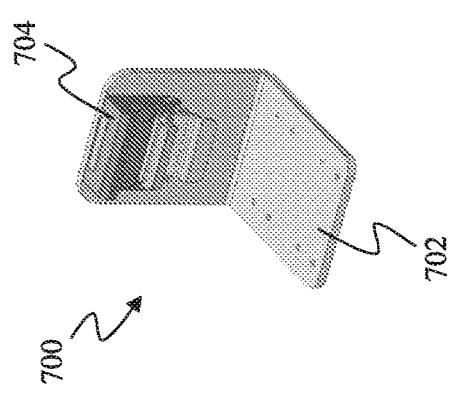
Fig. 7
Fig. 9

MEDICAL COMMUNICATION HUB AND ASSOCIATED METHODS

CROSS-REFERENCE TO RELATED APPLICATIONS

The present application is a continuation of U.S. patent application Ser. No. 14/238,026, filed Feb. 10, 2014, which is a U.S. national stage application Patent Cooperation Treaty Application No. PCT/US2012/052241, filed Aug. 24, 2012, which claims priority to and the benefit of U.S. Provisional Patent Application No. 61/526,990, filed Aug. 24, 2011,each of which is hereby incorporated by reference in its entirety.

TECHNICAL FIELD

Embodiments of the present disclosure relate generally to the field of medical devices and, more particularly, to a medical communication system and associated methods of use.

BACKGROUND

Innovations in diagnosing and verifying the level of success of treatment of disease have migrated from solely using external imaging processes to now including internal diagnostic processes as well. In particular, diagnostic equipment and processes have been developed for diagnosing vasculature blockages and other vasculature disease by means of ultra-miniature sensors placed upon the distal end of a flexible elongate member such as a catheter, or a guide wire used for catheterization procedures. For example, known medical sensing techniques include angiography, intravascular ultrasound (IVUS), forward looking IVUS (FL-IVUS), fractional flow reserve (FFR) determination, a coronary flow reserve (CFR) determination, optical coherence tomography (OCT), trans-esophageal echocardiography, and image-guided therapy. Each of these techniques may be better suited for different diagnostic situations. To increase the chance of successful treatment, health care facilities may have a multitude of imaging and sensing modalities on hand in a catheter lab during a procedure. However, each imaging modality in a catheter lab traditionally requires its own special-purpose diagnostic equipment. For instance, an imaging modality may require a catheter, a patient interface module (PIM), a user control interface, a display, a specialized power unit, and a processing unit such as a customized personal computer. Traditionally, all of this equipment is located in the catheter room itself during a procedure and depends on a substantial wiring infrastructure for data transport and dependable power. Physical space is typically at a premium in catheter labs and each additional imaging modality employed in a catheter lab complicates the pre-procedure setup and limits the movement of health care professionals during procedures. For example, typically, each additional imaging modality may require its own communication cable and its own power cable. These cable assemblies are often coiled under patient tables and are prone to being damaged from either being stepped on by personnel or equipment rolling over them. Cleaning the cables after a procedure is also very time consuming and difficult.

While the existing devices and methods have been generally adequate for their intended purposes, they have not been entirely satisfactory in all respects. The medical sensing systems and associated methods of the present disclosure overcome one or more of the shortcomings of the prior art.

SUMMARY

In one exemplary aspect, the present disclosure is directed to a powered medical communication hub. The hub includes a housing and a rear interface assembly disposed at a distal end of the housing. The rear interface assembly includes a first data link configured to transmit first medical data associated with a first modality to a processing system and a power link configured to receive a first amount of power. The hub also includes a power distribution module disposed within the housing, electrically coupled to the power link, and configured to convert the first amount of power into a plurality of power levels, and a forward interface assembly disposed at a proximal end of the housing, the forward interface assembly including a first connector communicatively coupled to the first data link and electrically coupled to the power distribution module, the first connector being configured to provide a first medical sensing device coupled thereto with a second amount of power equal to one of the plurality of power levels and receive the first medical data from the first medical sensing device.

In some instances, the housing may be fluid resistant and an interface between the rear interface assembly and the housing and an interface between the front interface assembly and the housing may be fluid resistant. Also, in some instances, the second amount of power may be different than the first amount of power. Additionally, in some instances, the front interface assembly may include a second connector electrically coupled to the power distribution module, the second connector being configured to provide a second medical sensing device coupled thereto with a third amount of power equal to one of the plurality of power levels and receive second medical data associated with a second modality different from the first modality from the second medical sensing device.

In another exemplary aspect, the present disclosure is directed to a medical communication system including a powered medical communication hub having a mounting portion thereon. The hub includes a plurality of connectors, each connector in the plurality of connectors being configured to receive medical data associated with a different medical sensing modality and to provide power to a medical sensing device coupled thereto and a rear interface assembly configured to receive a plurality of cables, the cables communicatively and electrically coupling the hub to a processing system. The system also includes mounting means releaseably coupled to the mounting portion of the powered medical communication hub, the mounting means being configured to mount the powered medical communication hub within a medical environment and a cable protection assembly releaseably coupled to the rear interface assembly of the powered medical communication hub, the plurality of cables extending through the cable protection assembly.

In some instances, the cable protection assembly may include an elongate and flexible housing enclosing the cables therein. Also, in other instances, the mounting means may include a rail clamp configured to releaseably couple to a rail in a medical environment. In yet another exemplary aspect, the present disclosure is directed to a method of collecting medical sensing data including receiving, at a powered medical communication hub, a first amount of power from a power source, converting, with a power distribution module in the powered medical communication hub, the first amount of power into a plurality of power levels, providing, with the powered medical communication hub, a second amount of power equal to one of the plurality of power levels to a first medical sensing device, receiving, at the powered medical communication hub, first medical data associated with a first modality from the first medical sensing device, and transmitting, with the powered medical communication hub, the first medical data to a processing system.

In some instances, the method of collecting medical sensing data may include providing, with the powered medical communication hub, a third amount of power equal to one of the plurality of power levels to a second medical sensing device, receiving, at the powered medical communication hub, second medical data associated with a second modality different from the first modality from the second medical sensing device, and transmitting, with the powered medical communication hub, the second medical data to the processing system.

In one exemplary aspect, the present disclosure is directed to a patient communication system. The patient communication system includes a first medical sensing device operable to collect first medical data associated with a first modality and an analog to digital converter communicatively coupled to the first medical sensing device and operable to digitize the first medical data. The system also includes a network communication module communicatively coupled to the first medical sensing device and a data network, the network communication module operable to transmit the digitized first medical data onto the data network. Further, the system includes a controller communicatively coupled to the analog to digital converter and the network communication module and operable route the first medical sensing data to the network communication module. The system also includes a power source operable to provide power to the first medical sensing device, the controller, and the network communication module.

In some instances, the patient communication system includes including a hub having therein the analog to digital converter, controller, and network communication module. Further, in some instances, the system includes a first patient isolation module communicatively coupled to the first medical sensing device and the hub and operable to receive the first medical data from the first medical sensing device and transmit the first medical data to the hub, the first patient isolation module being further operable to route power from the power source to the first medical sensing device.

In another exemplary aspect, the present disclosure is directed to a method of collecting medical sensing data. The method of collecting medical sensing data includes collecting, with a first medical sensing device, first medical data associated with a first modality and digitizing, with an analog to digital converter, the first medical data. The method also includes routing, with a controller communicatively coupled to the analog to digital converter, the digitized first medical data to a network communication module and transmitting, with the network communication module communicatively coupled to a data network, the digitized first medical data onto the data network. Further the method includes providing power, with a power source, to the first medical sensing device, the controller, and the network communication module.

In some instances, the digitizing with the analog to digital converter, the routing with the controller, the transmitting with the communication module, and the providing power with the power source are performed by a hub communicatively coupled to the first medical device. Further, in some instances, the collecting first medical data includes transmitting the first medical data through a first patient isolation module to the hub.

In another exemplary aspect, the present disclosure is directed to a patient communication system. The patient communication system includes a first control module operable to receive first medical data associated with a first modality from a first body sensing device and a second control module operable to receive second medical data associated with a second modality from a second body sensing device. The system further includes a first power module operable to dynamically supply a first amount of power to the first body sensing device based on a power requirement of the first body sensing device and a second power module operable to dynamically supply a second amount of power to the second body sensing device based on a power requirement of the second body sensing device. Further, the system includes a communication module operable to transmit the first and second medical data to a data network.

In another exemplary aspect, the present disclosure is directed to a method of using a patient communication system. The method of using a patient communication system includes coupling a first body sensing device to a first patient isolation module, the first body sensing device including a first sensor disposed thereon and coupling the first patient isolation module to a hub, the hub communicatively coupled to a data network. The method further includes coupling a second body sensing device to a second patient isolation module, the second body sensing device including a second sensor disposed thereon and coupling the second patient isolation module to the hub. Further, the method includes utilizing the first sensor to collect first medical characteristic data associated with a patient, the collecting including transmitting the first medical characteristic data to the hub and also utilizing the second sensor to collect second medical characteristic data associated with the patient, the collecting including transmitting the second medical characteristic data to the hub. The method also includes transmitting, with the hub, the first and second medical characteristic data to the data network and receiving, at a user interface, processed first and second medical characteristic data from the data network, the user interface being communicatively coupled to the hub.

BRIEF DESCRIPTION OF THE DRAWINGS

FIG. 7 is a diagrammatic perspective view of a horizontal rail mount.

FIG. 8 is a diagrammatic perspective view of a vertical rail mount.

FIG. 9 is a diagrammatic perspective view of a magnetic mounting system.

FIG. 10 is a diagrammatic perspective view of an angled mounting bracket.

DETAILED DESCRIPTION

Figure 1:
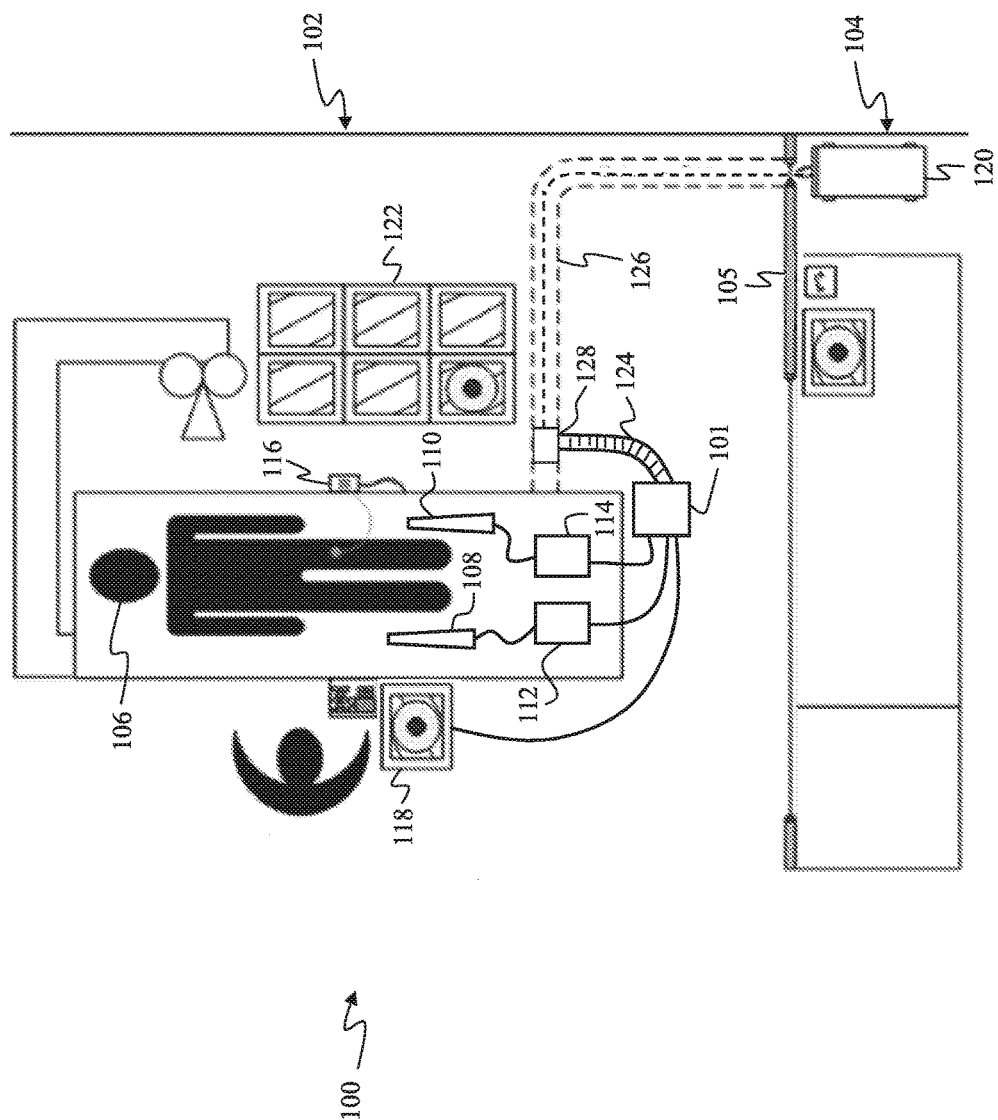
FIG. 1 is a schematic drawing depicting a medical sensing communication system including a powered medical communication hub according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications in the described devices, instruments, methods, and any further application of the principles of the disclosure as described herein are contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

FIG. 1 is a schematic drawing depicting a medical sensing communication system 100 including a powered medical communication hub 101. The medical sensing communication system 100 is a data collection solution for multiple modality medical sensing. Generally, in the system 100, the hub 101 is a central unit that connects to a plurality of medical sensing-related tools, distributes power to the plurality of tools, and facilitates communication between the tools and a processing workstation and/or data network. In one embodiment, the communication system 100 may be utilized to collect data from medical sensing devices and transmit it to computing resources, where it is processed and returned.

In the illustrated embodiment, the medical sensing communication system 100 is deployed in a catheter lab 102 having a separate control room 104 isolated by an intervening wall 105. In other embodiments, however, the medical sensing communication system 100 may be deployed in an operating room, diagnostic room, or other medical environment used to perform any number of patient procedures. The catheter lab 102 includes a sterile field but its associated control room 104 may or may not be sterile depending on the requirements of a procedure and/or health care facility. The catheter lab and control room may be used to perform on a patient any number of medical sensing procedures such as angiography, intravascular ultrasound (IVUS), virtual histology (VH), forward looking IVUS (FL-IVUS), intravascular photoacoustic (IVPA) imaging, a fractional flow reserve (FFR) determination, a functional measurement determination, a coronary flow reserve (CFR) determination, optical coherence tomography (OCT), computed tomography, intracardiac echocardiography (ICE), forward-looking ICE (FLICE), intravascular palpography, transesophageal ultrasound, or any other medical sensing modalities known in the art. For example, in catheter lab 102 a patient 106 may be undergoing a multi-modality procedure, in which IVUS data will be collected with an IVUS catheter 108 and OCT data will be collected with an OCT catheter 110. The IVUS catheter 108 may include one or more sensors such as a phased-array transducer. In some embodiments, the IVUS catheter 108 may be capable of multi-modality sensing such as IVUS and IVPA sensing. The OCT catheter 110 may include one or more optical sensors.

The communication system 100 includes a number of interconnected medical sensing-related tools in the catheter lab 102 and control room 104 to facilitate this multi-modality workflow procedure, including an IVUS patient interface module (PIM) 112, an OCT PIM 114, an electrocardiogram (ECG) device 116, a bedside control surface 118, a processing system 120, and a boom display 122. The hub 101 in the catheter lab 102 consolidates the multitude of cables extending from these medical sensing-related tools and communicatively couples them to the processing system 120. That is, the hub 101 is an intermediary through which the tools in the catheter lab 102 connect to the processing system 120. In general, the hub 101 is coupled to the processing system 120 via a plurality of power and communication cables. To alleviate the problems associated with loose cabling in a crowded medical working environment, the cables coupling the hub 101 to the processing system 120 extend through a protective hose 124 and a trench 126 in the floor of the catheter lab 102. The cables enter the trench 126 through a trench entry port 128. In this manner, the cables are aggregated and protected the entirety of the distance from the hub 101 to the processing system 120. Of course, the cabling between the hub 101 and processing system 120 may be oriented in many other configurations depending on the specific catheter lab configuration. For instance, the cabling may extend through the protective hose 124 and enter a wall or a ceiling through a termination plate before travelling to the processing system. In the illustrated embodiment, the hub 101 is mounted on the floor near the patient 106 to reduce the amount of cabling located in high-traffic areas near the patient. In some instances, the hub 101 may be located in the sterile field surrounding the patient 106. The hub 101 and its associated cabling and mounting solutions will be described in greater detail in association with FIGS. 2-12.

In the illustrated embodiment, the processing system 120 is a computer workstation with the hardware and software to acquire, process, and display multi-modality medical sensing data, but in other embodiments, the processing system 120 may be any other type of computing system operable to process medical data or assist in computer aided surgery (CAS). In the embodiments in which processing system 120 is a computer workstation, the system includes at least a processor such as a microcontroller or a dedicated central processing unit (CPU), a non-transitory computer-readable storage medium such as a hard drive, random access memory (RAM), and/or compact disk read only memory (CD-ROM), a video controller such as a graphics processing unit (GPU), and a network communication device such as an Ethernet controller. U.S. Patent Application No. 61/473,570, entitled "MULTI-MODALITY MEDICAL SENSING SYSTEM AND METHOD", discloses a computing resource capable of processing multi-modality medical sensing data and is hereby incorporated by reference in its entirety.

As mentioned above, the ECG device 116 is also communicatively coupled to hub 101 via a wired or wireless connection. The ECG device 116 is operable to transmit electrocardiogram signals from patient 106 to the hub 101. In some embodiments, the hub 101 may be operable to synchronize data collection with the catheters 108 and 110 using the ECG signals from the ECG 116.

The bedside control surface 118 is also communicatively coupled to the hub 101 and provides user control of the particular medical sensing modality (or modalities) being used to diagnose the patient 106. In the current embodiment, the bedside control surface 118 is a touch screen that provides user controls and diagnostic images on a single surface. In alternative embodiments, however, the bedside control surface 118 may include both a non-interactive display and separate controls such as physical buttons and/or a joystick. In the illustrated embodiment, the bedside control surface 118 and hub 101 communicate over a wired connection such as a standard copper link but, alternatively, the control surface 118 and hub 101 may communicate wirelessly. The bedside control surface 118 includes an integrated processing unit to drive a graphical user interface (GUI)-based workflow presented on the touch screen. U.S. Patent Application No. 61/473,591, entitled "DISTRIBUTED MEDICAL SENSING SYSTEM AND METHOD" and filed on Apr. 8, 2011, discloses a bedside control surface that executes GUI-based workflows using a software framework and is hereby incorporated by reference in its entirety.

The system 100 further includes a boom display 122. The boom display 122 may include one or more monitors capable of displaying information associated with a medical sensing procedure. In the illustrated embodiment, the boom display 122 is coupled to, powered, and driven by the hub 101.

Figure 2A:
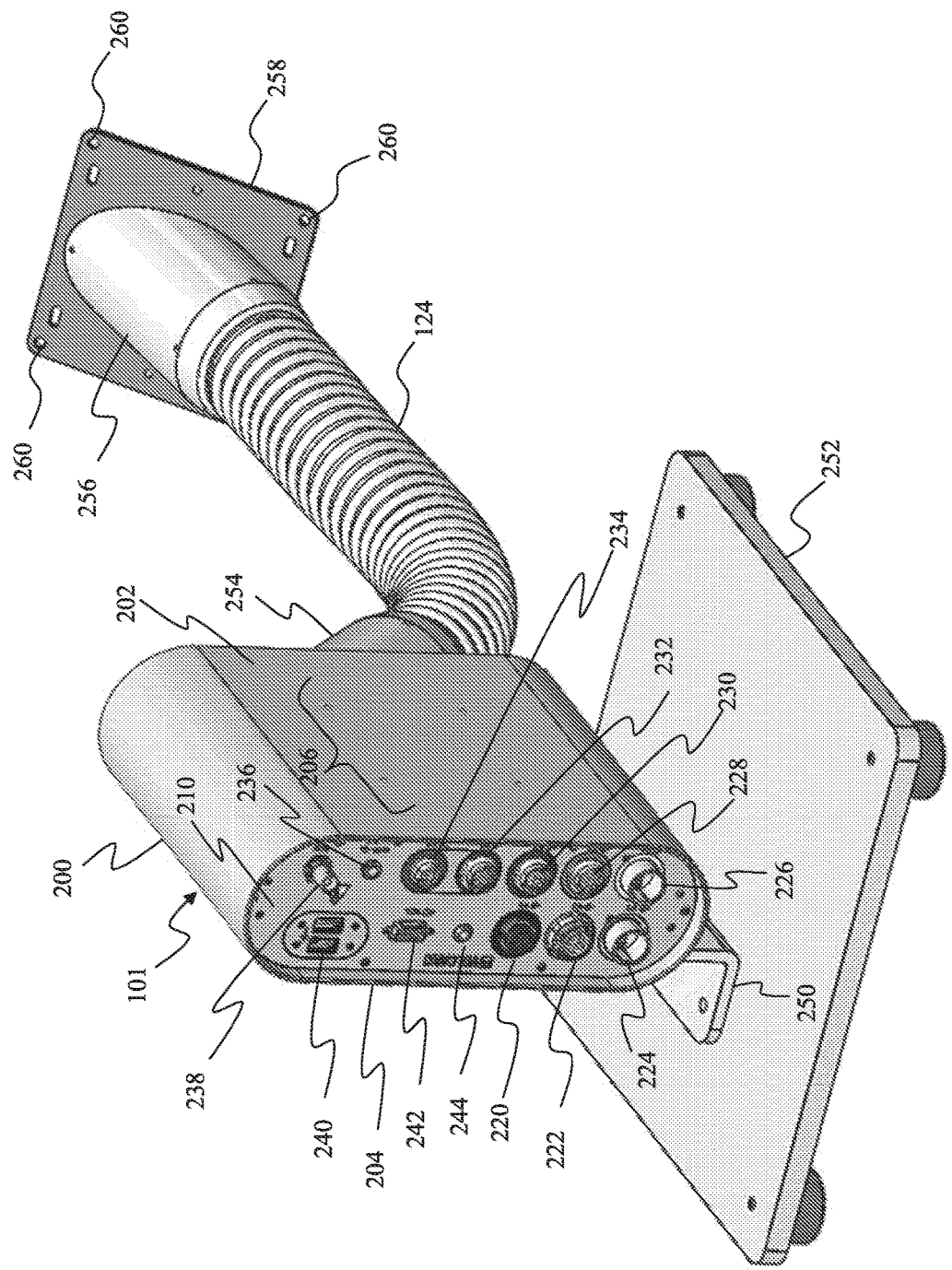
FIG. 2A is a diagrammatic front perspective view of the powered medical communication hub of FIG. 1 installed in a catheter lab.
Figure 2B:
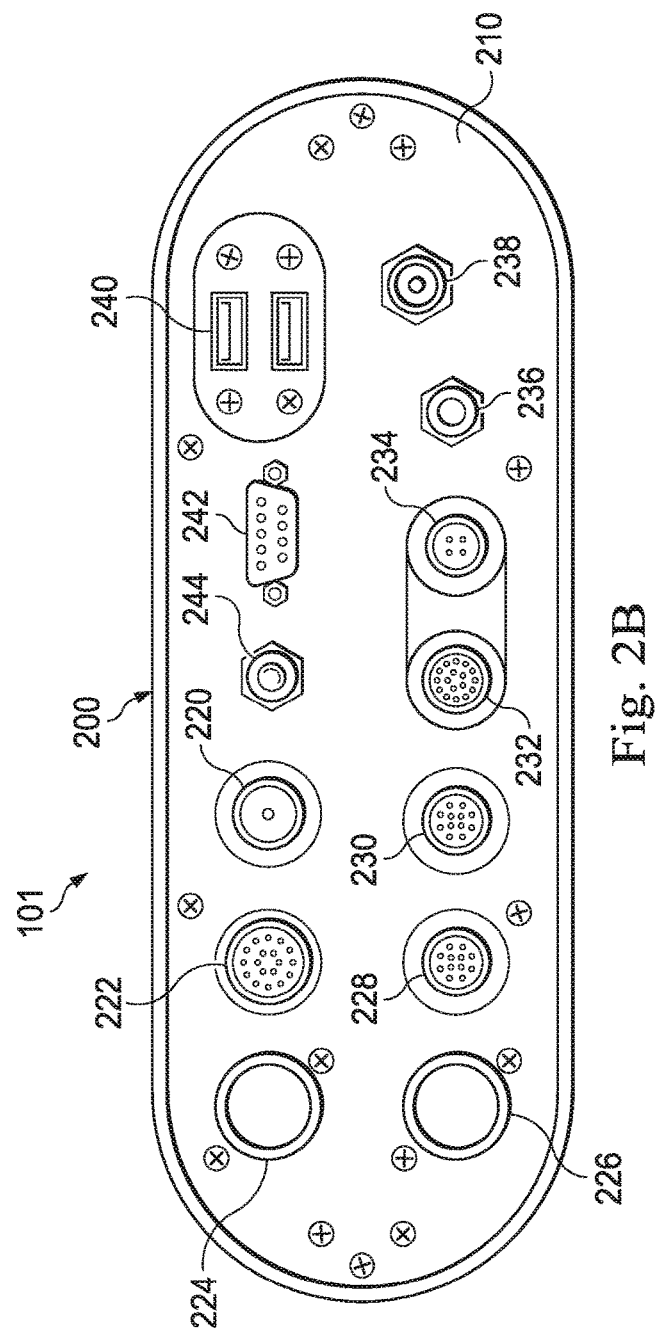
FIG. 2B is a diagrammatic front close-up view of the powered medical communication hub of FIG. 1.
Figure 3:
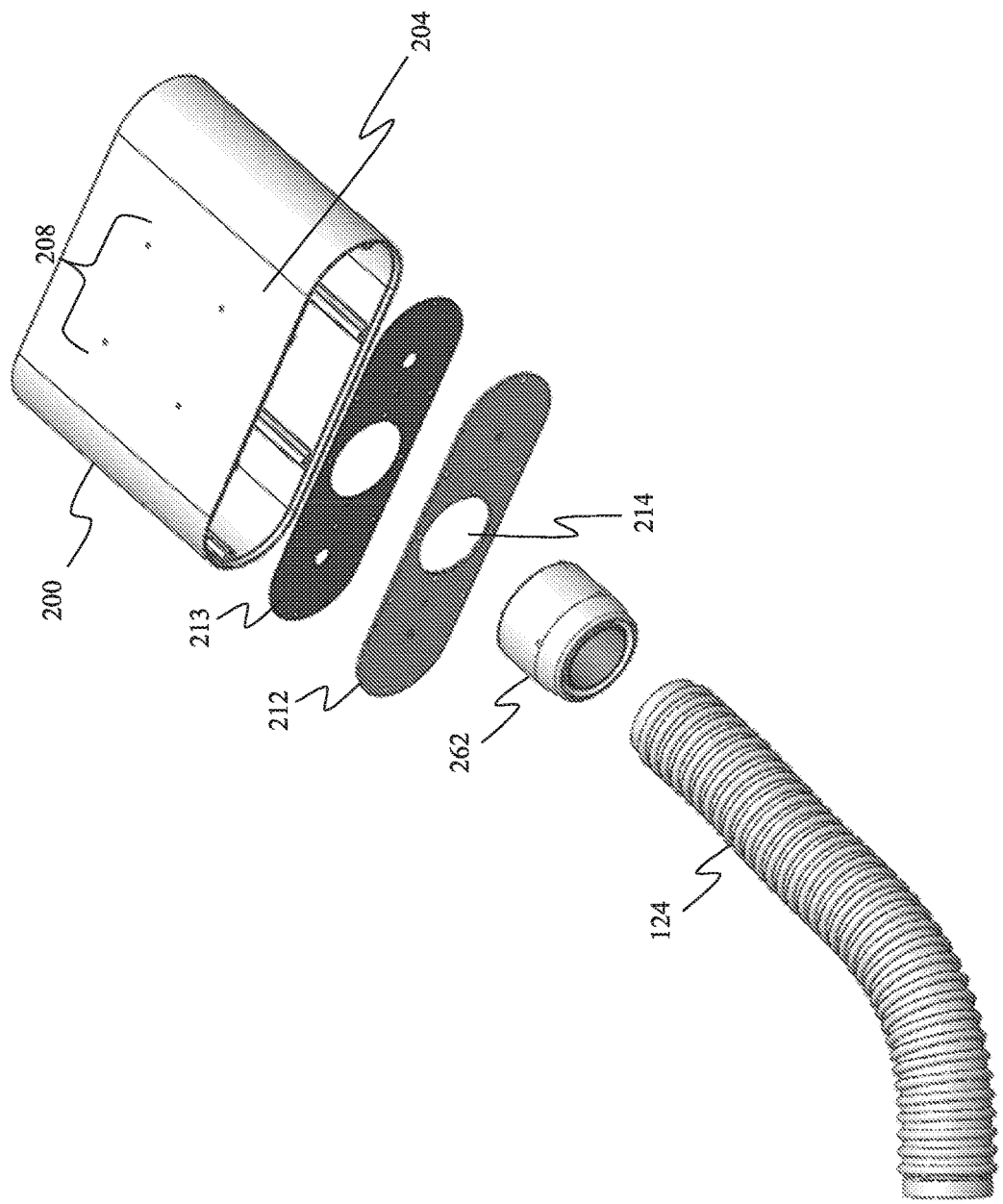
FIG. 3 is a diagrammatic rear perspective exploded view of portions of the powered medical communication hub of FIG. 1.

With reference now to FIGS. 2A, 2B, and 3, illustrated is an aspect of the medical sensing communication system 100. Specifically, FIG. 2A is a diagrammatic front perspective view of the powered medical communication hub 101 of FIG. 1 installed in a medical environment such as catheter lab 102, and FIG. 2B is a diagrammatic front close-up view of the hub 101. FIG. 3 is a diagrammatic rear perspective exploded view of portions of the hub 101. As mentioned above, the hub 101 is a intermediary through which the medical sensing-related tools receive power and communicate with processing system 120. In one general aspect, the hub 101 is operable to provide power and instructions to medical sensing devices and transfer medical sensing data from connected medical sensing devices such as the IVUS PIM 112 and OCT PIM 114 to remote computing resources such as processing system 120 to be processed. Once processed, the medical sensing data may be returned to the hub 101, where it is routed to the control surface 118 and boom display 122 to be displayed and analyzed by clinicians.

The hub 101 includes a cylinder-like housing 200. In the illustrated embodiment, the housing 200 is constructed of a impact-resistant and fluid-resistant metal and has a height of approximately 3.5 inches, a width of approximately 10 inches, and a depth of approximately 8 inches. In alternative embodiments, the housing 200 may be constructed of a different suitable material and/or be of different dimensions. The housing 200 includes a bottom mounting surface 202 and a top mounting surface 204, both of which are planar. The bottom mounting surface 202 includes a set of threaded mounting apertures 206 and the top mounting surface 204 includes a set of threaded mounting apertures 208. As will be described in association with FIGS. 7-10, any number of mounting brackets may be releaseably coupled to the housing 200 using either set of threaded mounting apertures 206 and 208. In the illustrated embodiment, each set of mounting apertures is configured to conform to the Video Electronics Standards Association (VESA) MIS-D hole mount pattern. In alternative embodiments, the mounting apertures 206 and 208 may conform to a different standard or may conform to a proprietary pattern. Further, the mounting surfaces 202 and 204 may alternatively include different mounting solutions such as channels, slots, clips, or magnetic elements.

The hub 101 further includes a front interface panel 210 coupled to the front of the housing 200 and a rear interface panel 212 coupled to the rear of the housing 200. Each of the interface panels 210 and 212 includes a complementary gasket 213 disposed on the side facing the housing 200 such that when they are secured to the housing 200 as shown in FIG. 2A they create a fluid-resistant seal. The gaskets 213 may be formed of rubber, silicone, or other sealing material. In one embodiment, the hub 101 may have a rating of IPX4 against fluid ingress as defined by the International Electrotechnical Commission (IEC) standard 60529.In other embodiments in which the hub may be used in different environments, the hub may have a different fluid ingress rating. As shown in FIG. 3, the rear interface panel 212 includes a cable aperture 214 through which cables extending from the hub 101 to the processing system 120 may pass. As shown in FIG. 2B, the front interface panel 210 of the hub 101 includes a plurality of connectors to which a plurality of medical sensing-related tools may connect. In the illustrated embodiment, the front panel 210 includes: an IVUS PIM connector 220 with conductive contacts configured to transfer power, ground, data, and control signals; a functional measurement (FM) tool connector 222 with conductive contacts configured to transfer power, ground, data and control signals; an first fiber optic connector 224 and a second fiber optic connector 226 each configured to pass power, ground, and light-based data signals; an OCT PIM connector 228 with conductive contacts configured to transfer 48 volts DC, ground, and Ethernet-based data; a bedside control surface connector 230 with conductive contacts configured to transfer 12 volts DC, ground, and Ethernet-based data; a FLIVUS PIM connector 232 with conductive contacts configured to transfer 48 volts DC, ground, and Universal Serial Bus (USB)-based data; and a FLIVUS footswitch connector 234 with conductive contacts configured to transfer foot-actuated control signals. The connectors 220, 222, 228, 230, 232, and 234 are push-pull ring style connectors that are configured to allow for one-handed connection and disconnection of cables. Further, the connectors are fluid-resistant (sealed), color-coded for easy identification, and keyed differently, for example in shape and pin-count, so as prevent misconnected cables. For example, as shown in FIG. 2B, the FM tool connector includes 18 pin holes in a circular configuration, but the bedside control surface connector includes 12 pin holes in a linear configuration. In the illustrated embodiment, the connectors 228, 230, 232, and 234 are JBX series connectors commercially available from Souriau SAS of Versailles, France. However, in alternative embodiments, other commercially-available or proprietary connectors may be utilized and the connectors may be configured to include any number of additional features. Although the connectors 220, 222, 224, 226, 228, 230, 232, and 234 as-labeled are associated with specific modalities, it is contemplated that medical tools associated with additional and/or different modalities may connect to one or more of the connectors provided that the medical tools' connectors are compatible (i.e. number of pins, shape).

The front panel 210 further includes an auxiliary power connector 236 configured to provide 24 volts DC, a ECG/aortic device connector 238, two USB connectors 240, and a VGA display connector 242. In one catheter lab configuration, the auxiliary power connector 236 may provide power and the VGA display connector 242 may provide a video signal to a bedside display monitor such as the boom display 122. Further, the USB connectors 240 may couple to and receive control signals from bedside controller devices such as joysticks, touchpads, hand gesture/motion capture input devices, or any other suitable controller devices. In the illustrated embodiment, because the USB connectors 240 and the VGA display connector 242 are standardized, it is contemplated that any number of USB-based and VGA-based tools may communicate with the processing system 120 via the hub 101. Additionally, the USB connectors 240 may be fluid-resistant. Further, in alternative embodiments, the VGA display connector 242 may be another type of display connector such as a DVI connector, an HDMI connector, a DisplayPort connector, an S-Video connector, or other video-based connector, and the USB connectors 240 may be other types of data ports such as IEEE 1394 (FireWire), Thunderbolt, serial, parallel, eSATA, or proprietary connectors. Additionally, the front panel 210 includes an LED indicator 244 configured to indicate when the hub 101 is powered on. The front interface panel 210 and the connectors 220, 222, 224, 226, 228, 230, 232, 234, 236, 238, 240, and 242 may together be considered a forward interface assembly.

As mentioned above, FIG. 2A shows the hub 101 installed in one example configuration in a medical environment such as catheter lab 102. Specifically, a vertical mounting bracket 250 is coupled to the top mounting surface 204 via the set of threaded mounting apertures 208. The mounting bracket 250 is in turn mounted to a floor stand 252, which is configured to sit on the floor of a catheter lab with a plurality of stabilizing feet. Further, cables extending from the hub 101 to the processing system 120 exit the hub 101 through the aperture 214 in the rear panel 212 and extend through an angled coupler 254, the flexible protective hose 124, a second angled coupler 256, and an aperture in a termination plate 258. The angled coupler 254 releaseably couples to the rear panel 212 and includes a rubber seal around its periphery such that when it is coupled to the panel the interface between the coupler and the panel is fluid-resistant. The flexible protective hose 124 is configured to protect the cables extending therethrough and may be resistant to bodily fluids and cleaning chemicals typically found in medical environments. The flexible protective hose 124 is further pliable such that it may be routed in a convenient manner in a catheter lab. The termination plate 258 includes an aperture sized to approximately match the diameter of the second angled coupler 256, and also includes a set of mounting apertures 260 configured in a standardized pattern on the face of the plate. The mounting apertures 260 permit the plate 258 to be mounted around an aperture (e.g. a wall exit point, floor exit point, etc) through which the hub-connected cables exit the catheter lab. In the illustrated embodiment, the termination plate 258 and the set of mounting apertures 260 conform to the GE Termination standard. However, in other embodiments, the termination plate 258 and apertures 260 may conform to another standard such the Phillips Termination standard, the double gang standard, or the single gang standard. As shown in FIG. 3, a straight coupler 262 may also be releaseably coupled to the rear panel 212 and the flexible protective hose 124. The straight coupler 262 directs the protective hose 124 away from the hub 101 at a different angle than the angled coupler 254 to provide for additional placement options in a catheter lab or other medical environment. The angled coupler 254 or straight coupler 262, flexible protective hose 124, and second angled coupler 256 may together be considered a cable protection assembly.

Figure 4:
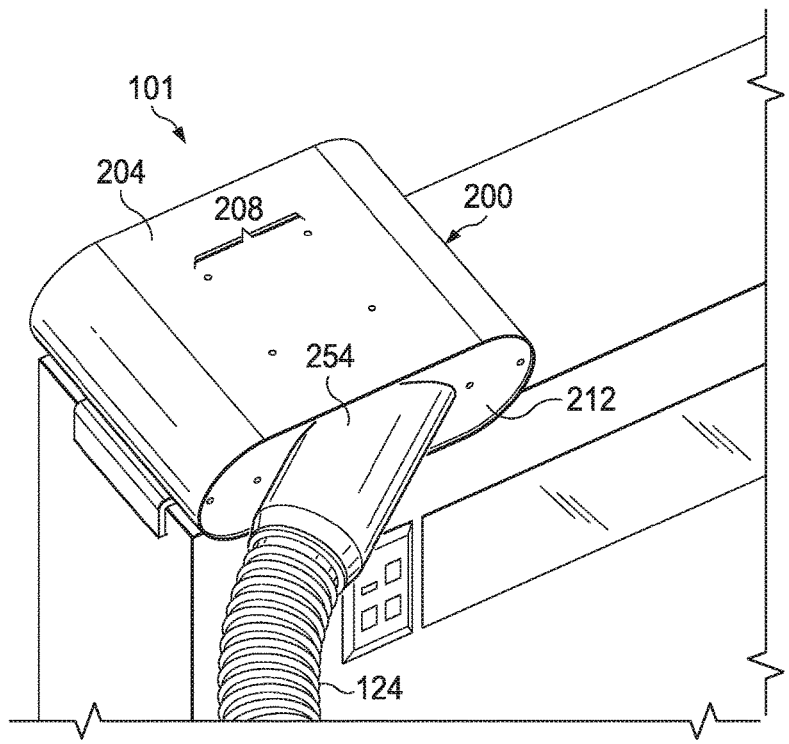
FIG. 4 is a rear perspective view of a powered medical communication hub with an angled coupler attached thereto.
Figure 5:
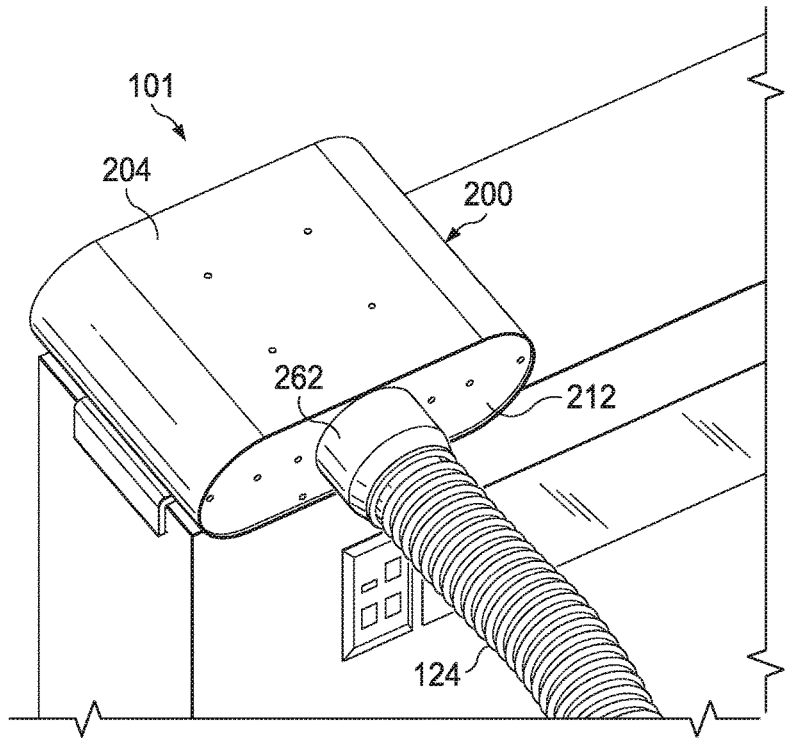
FIG. 5 is a rear perspective view of a powered medical communication hub with a straight coupler attached thereto.
Figure 12:
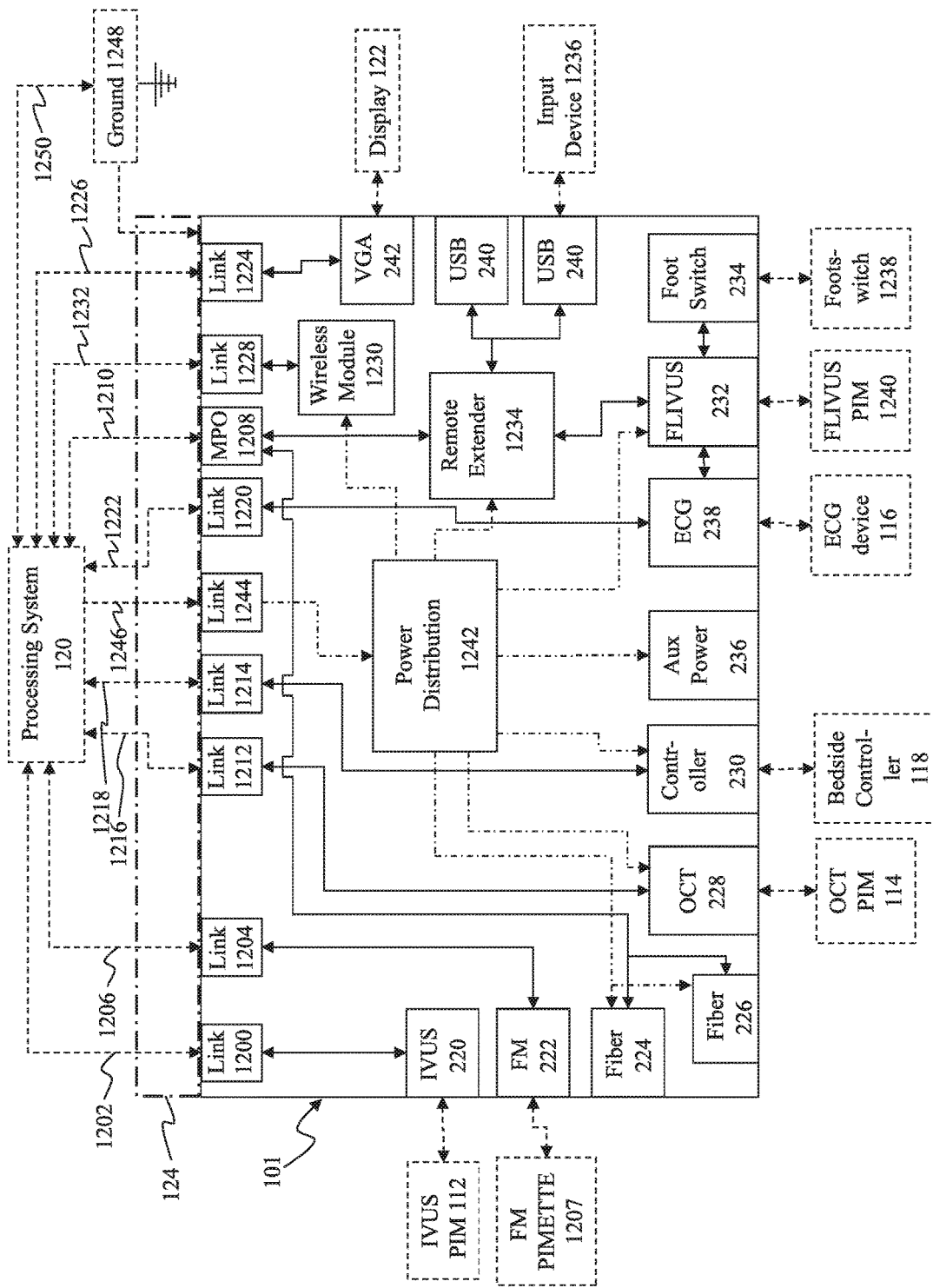
FIG. 12 is a functional block diagram of an embodiment of a powered medical communication hub.

With reference now to FIGS. 4 and 5, illustrated are different configurations of the medical communication system 100 in a medical environment. Specifically, FIG. 4 is a rear perspective view of the hub 101 with the angled coupler 254 coupled to the rear panel 212, and FIG. 5 is a rear perspective view of the hub 101 with the straight coupler 262 coupled to the rear panel 212. As shown by FIGS. 4 and 5, the couplers 254 and 262 direct the flexible protective hose 124 away from the hub 101 at different angles. As shown, all cable-based connections to the rear of the hub 101 including power and communications are contained within the flexible hose 124. Examples of the cables exiting the rear of the hub 101 within the hose 124 are shown in FIG. 12.

Figure 6:
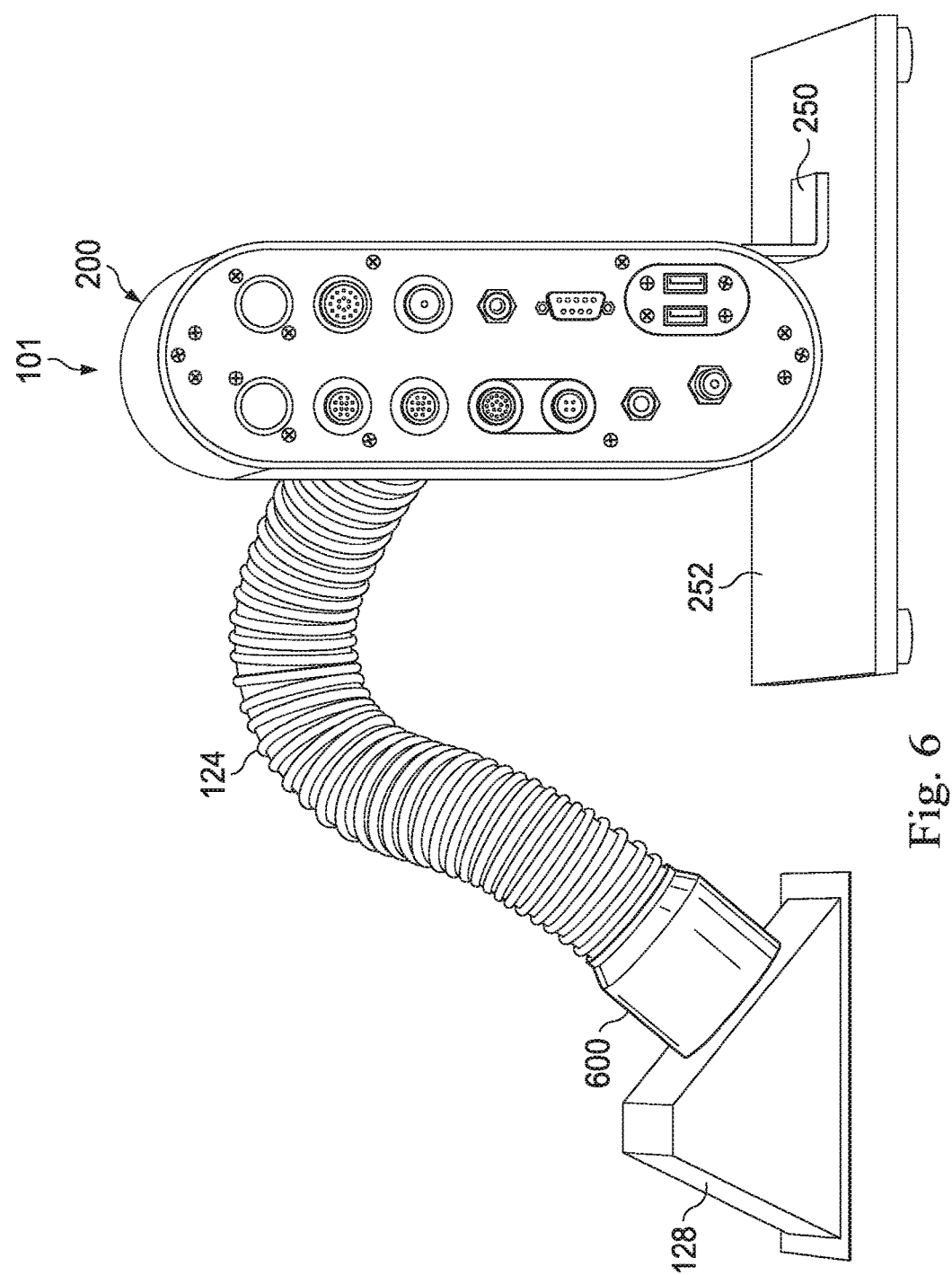
FIG. 6 is a diagrammatic front perspective view of an aspect of a medical communication system installed in a medical environment.

FIG. 6 is a diagrammatic front perspective view of an aspect of the medical communication system 100 installed in a medical environment. Specifically, the hub 101 is mounted to the floor stand 252 and flexible protective hose 124 extends from the rear panel 212 to a straight coupler 600 which is coupled to the trench entry port 128. In some embodiments, the trench entry port 128 includes a second aperture (not shown) disposed on the side opposite of the straight coupler 600. This second aperture may be used to pass additional cables from the catheter lab into the trench below.

With reference now to FIGS. 7-10, illustrated are four mounting brackets that may be coupled to the hub 101 so that the hub may be dynamically mounted in a medical environment such as catheter lab 102. FIG. 7 is a diagrammatic perspective view of a horizontal rail mount 700. The horizontal rail mount 700 includes a mounting surface 702 that is configured to couple to either the bottom mounting surface 202 or the top mounting surface 204 on the hub 101. The mounting surface 702 includes a set of mounting apertures that align with either the set of mounting apertures 206 or 208 on the hub 101. In the illustrated embodiment, the set of mounting apertures on the mounting surface 702 conforms to the VESA hole mount pattern, but, alternatively, may be configured to conform to a different pattern depending on the pattern implemented on the mounting surfaces of the hub 101. When the mounting apertures on the mounting surface 702 are aligned with either the set of mounting apertures 206 or 208 on the hub 101, connectors such as screws nay pass through the aligned apertures and releaseably couple the horizontal rail mount 700 to the hub 101. The horizontal rail mount 700 further includes a rail clamp 704 that is configured to releaseably couple to a rail on or near a patient table in a catheter lab. In the illustrated embodiment, the rail clamp 704 is physically configured to mate with a standardized rail, and when the clamp is so mated, the attached hub 101 will be in a horizontal position. FIG. 8 is a diagrammatic perspective view of a vertical rail mount 800 that is configured to be coupled to the hub 101. Specifically, the vertical rail mount 800 is similar to the horizontal rail mount 700 in that it has a mounting surface 802 with a set of standardized mounting apertures and a rail clamp 804. However, when the hub 101 is coupled to the mounting surface 802 and the rail clamp 804 is clamped to a patient table rail, the hub 101 will be in a vertical position.

FIG. 9 is a diagrammatic perspective view of a magnetic mounting system 900 configured to allow the hub 101 to be mounted in a variety of locations around a catheter lab. The mounting system 900 includes a magnetic mount plate 902 with magnets disposed therein. The magnetic mount plate 902 is configured to releaseably couple to either the bottom mounting surface 202 or the top mounting surface 204 on the hub 101 via a set of mounting apertures that align with the mounting apertures on the hub. The magnetic mounting system 900 further includes a receiver plate 904 that may be mounted to a wall, floor, ceiling or any other flat surface in a catheter lab. The receiver plate 904 is configured to receive the mount plate 902 and hold it in place via magnetic force.

FIG. 10 is a diagrammatic perspective view of an angled mounting bracket 1000 that is configured to couple to the hub 101. The angled mounting bracket 1000 includes a mounting surface 1002 that is configured to be releaseably coupled to either the bottom mounting surface 202 or the top mounting surface 204 on the hub 101 via a set of mounting apertures that align with the mounting aperture on the hub. The angled mounting bracket 1000 further includes an angled surface 1004 configured to fit flush against and releaseably couple to a right angled surface in a catheter lab or other medical environment. For instance, the angled mounting bracket 1000 may be affixed to a corner of a gas box disposed under a patient table.

Figure 11A:
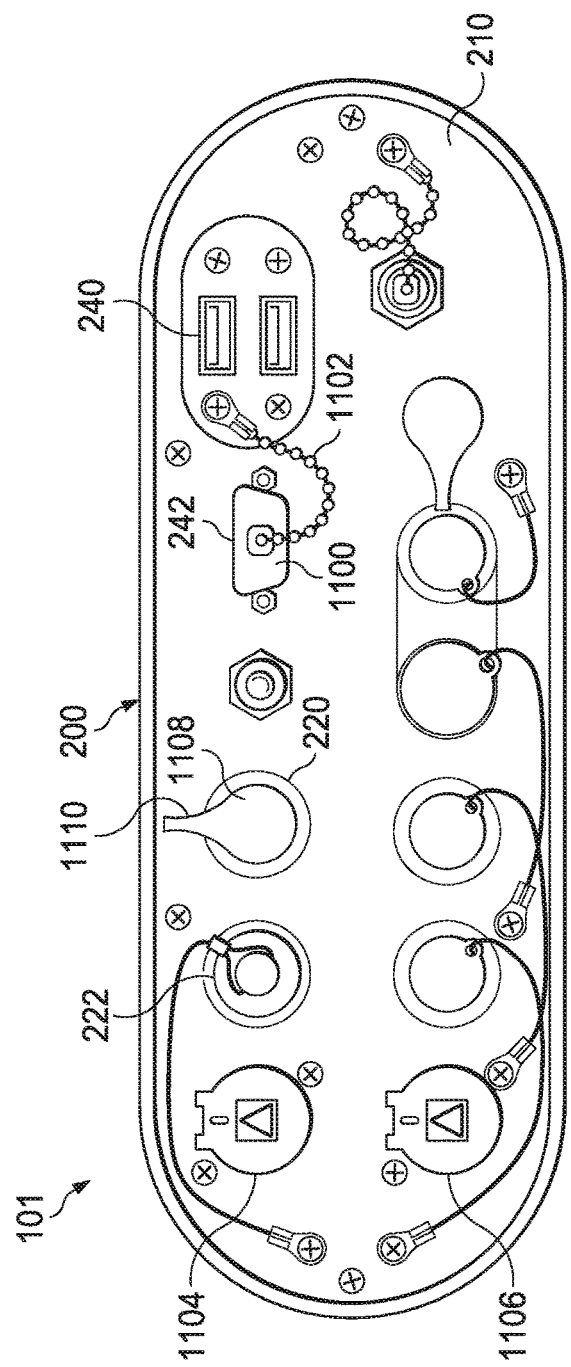
FIG. 11A is a front view of a powered medical communication hub in a fluid-resistant configuration.

FIG. 11A is a front view of the hub 101 in a fluid-resistant configuration. Specifically, as shown in FIG. 11A, a plurality of protective caps are disposed over the connectors on the front panel 210 to prevent fluid or foreign substances from entering the connectors. As mentioned above in association with FIGS. 2A and 2B, many of the connectors on the front panel 210 are sealed to provide some resistance against fluid ingress, but the illustrated caps provide further protection. It is contemplated that the caps shown in FIG. 11A may remain on their respective connectors during a patient procedure if their respective connectors are not in use. In the illustrated embodiment, the caps are commercially available from Souriau SAS, but alternatively, they may be any other type of cap configured to seal the connectors on the hub 101. Each cap is physically configured to mate with a specific connector so that the resulting seal is water-tight. For example, a trapezoid-shaped dust cap 1100 is disposed over the VGA connector 242. The dust cap 1100 includes a lanyard 1102 extending from the dust cap to the front panel 210. As another example, the fiber optic connectors 224 and 226 include flip caps 1104 and 1106 that are mounted to the connectors on hinges. As such, the flip caps 1104 and 1106 may be flipped open when cables need to be connected to the fiber optic connectors 224 and 226, and flipped close when the cables are disconnected. As mentioned above, the USB connectors 240 are sealed and are fluid-resistant, and thus do not require extra protection. As yet another example, in the illustrated embodiment of FIG. 11A, the circular-shaped IVUS PIM connector 220 has a circular-shaped protective cap 1108 disposed thereon. The protective cap 1108 is tethered to the connector 220 via a flexible arm 1110.

Figure 11C:
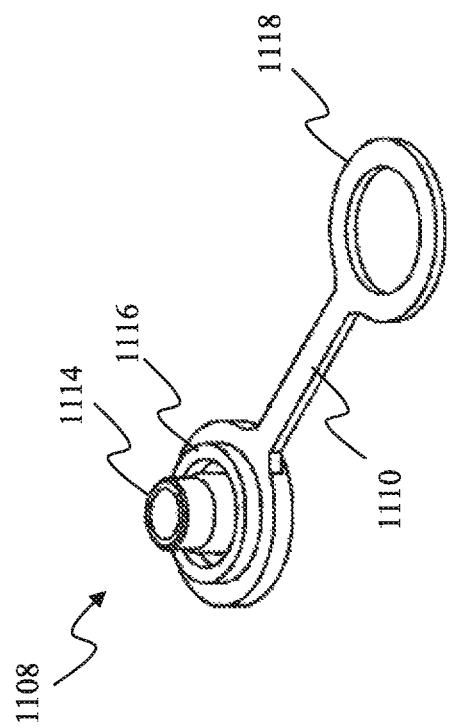
FIG. 11C is a diagrammatic perspective view of a protective cap according to various aspects of the present disclosure.
Figure 11B:
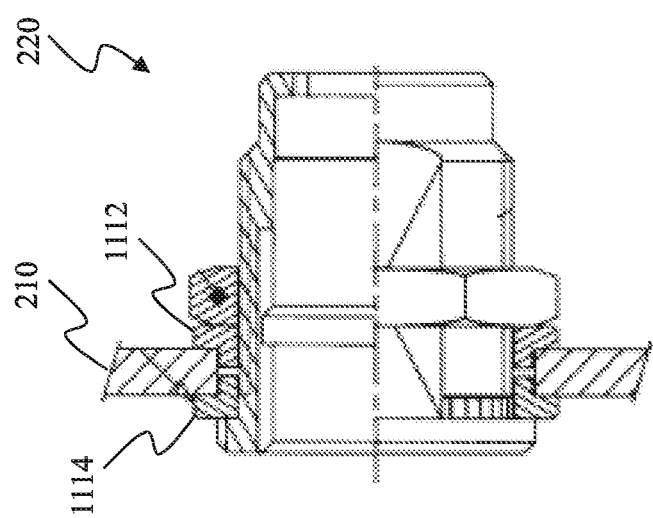
FIG. 11B is a diagrammatic sectional side view of a connector on a front panel of the powered medical communication hub of FIG. 11A.

Referring now to FIGS. 11B and 11C, FIG. 11B is a diagrammatic sectional side view of the IVUS PIM connector 220 on the front panel of the hub 101, and FIG. 11C is a diagrammatic perspective view of the protective cap 1108. As noted above, the interface between the front interface panel 210 and the connector 220 is fluid resistant. This is due in part to a pair of complementary washers 1112 and 1114. The washers 1112 and 1114 are disposed around the connector 220 on either side of the front panel 210 to create a fluid-resistant seal therebetween. As shown in FIG. 11C, the protective cap 1108 is configured to removeably mate with the connector 220 to keep dust, fluid, and other particles out of the connector. The cap 1108 includes an inner ring 1114 and an outer ring 1116 that are configured to create a fluid-resistant seal when engaged with the connector 220. The cap 1108 also includes a retaining portion 1118 configured to fixedly engage an outside portion of the connector 220. When so engaged, the cap 1108 is tethered to the connector 220 via the flexible arm 1110. The cap 1108 is just one example of a protective cap that may be used with the connectors on the hub 101 and other caps may be used that are configured in a different manner, for instance, to mate with connectors with different shapes than the connector 220.

FIG. 12 is a functional block diagram of an embodiment of a powered medical communication hub. As shown in FIG. 2A, the hub 101 may include the IVUS PIM connector 220, the functional measurement (FM) tool connector 222, the first and second fiber optic connector 224 and 226, the OCT PIM connector 228, the bedside control surface connector 230, the FLIVUS PIM connector 232, the FLIVUS footswitch connector 234, the auxiliary power connector 236, the ECG/aortic device connector 238, the USB connectors 240, and the VGA display connector 242. As shown in FIG. 12, the IVIS PIM connector 220 is communicatively coupled to the processing system 120 via a link 1200. A cable 1202 transmitting power, ground, and data signals extends from the processing system 120 to the link 1200, where the signals are internally forwarded to the IVUS PIM connector 220. In some embodiments, the link 1200 and the connector 220 may be integrated such that the cable 1202 running from the processing system 120 to the hub 101 extends through the aperture 214 in the rear panel 212 (FIG. 3) and couples to one side of the connector 220/link 1220, and a cable running from the IVUS PIM 112 to the hub 101 couples to the other side of the connector 220. In other embodiments, however, the link 1200 may be integrated into the rear panel 212 such that the cable 1202 running from the processing system 120 to the hub 101 does not extend into the interior of the hub. The hub 101 further includes a link 1204 that communicatively couples the processing system 120 to the FM tool connector 222. A cable 1206 transmitting power, ground, and data signals extends from the processing system 120 to the link 1204, where the signals are internally forwarded to the FM tool connector 222, which forwards the signals to a connected FM tool, such as a FM Pimette 1207. Similar to the link 1200, the link 1204 may, in some embodiments, be integrated into the FM connector 222 or, alternatively, it may be disposed on the rear panel 212.

The hub 101 further includes a MultiFiber Push-On (MPO) link 1208 to which the first and second fiber optic connectors 224 and 226 are internally coupled. In general, the MPO link 1208 is configured to aggregate fiber optic signals and route them over a single fiber optic line. As shown in FIG. 12, a single fiber optic cable 1210 extends from the processing system 120, through the aperture 212 in the rear panel 214, and to the MPO link 1208 where data destined for the first and second fiber optic connectors 224 and 226 is parsed and routed to the appropriate connector. In some embodiments, the MPO link 1208 may be coupled to a printed circuit assembly (PCA) disposed inside of the hub 101 near the aperture 214, but, in other embodiments, the MPO link may be disposed on the rear panel 212.

The hub 101 includes links 1212 and 1214 that respectively communicatively couple the processing system 120 to the OCT PIM connector 228 and the bedside control surface connector 230. As mentioned above, the connectors 228 and 230 pass Ethernet-based data signals to connected medical-sensing tools. Thus, in the illustrated embodiment, the links 1212 and 1214 are RJ45 jacks that respectively accept Cat 5e cables 1216 and 1218. However, in other embodiments, the links 1212 and 1214 may accept Ethernet-based data over coaxial, fiber optic, or some other type of suitable cable. In some embodiments, the links 1212 and 1214 may be integrated into a PCA disposed within the hub 101 and communicatively coupled to the connectors 228 and 230 via conductive traces on the PCA, but, in other embodiments, the links 1212 and 1214 may be disposed on the rear panel 212 for easy access. The hub 101 further includes a link 1220 configured to communicatively couple the processing system 120 to the ECG device connector 238, and thus the ECG device 116. In some embodiments, the link 1220 may be integrated into the ECG device connector 238 such that a ECG-signal cable 1222 running from the processing system 120 to the hub 101 extends through the aperture 214 in the rear panel 212 and couples to one side of the connector 238/link 1220, and a cable running from the ECG device 116 to the hub 101 couples to the other side of the connector 238. But, in other embodiments, the link 1220 may be disposed on the rear panel 212 such that the cable 1222 running from the processing system 120 to the hub 101 does not extend into the interior of the hub. Additionally, the hub 101 includes a link 1224 configured to communicatively couple the processing system 120 to the VGA connector 242 and pass video information to the display 122. In the illustrated embodiment, the link 1224 accepts a male VGA connector disposed on the end of a cable 1226 coupled to the workstation 120. However, in other embodiments, the link 1224 may be configured to accept other video-based connectors such as a DVI connector, an HDMI connector, a DisplayPort connector, or an S-Video connector. Similar to the links 1200, 1204, and 1220, the link 1224 may, in some embodiments, be integrated into the its associated connector 242 or, alternatively, it may be disposed on the rear panel 212 for easy access.

The hub 101 further includes a link 1228 and a wireless communication module 1230 that is operable to communicate with medical sensing-related tools in close proximity to the hub, such as a wireless-ready PIM. In one embodiment, the wireless communication module 1230 may be a wireless personal area network (WPAN) communication module such as an Ultra-wide band (UWB) module, a wireless FireWire module, or wireless USB module, a Bluetooth module, a IEEE 802.11-based wireless module or some other high-speed wireless module. In the illustrated embodiment, data passes over a data cable 1232 to link 1228, which forwards it to the wireless communication module 1230 to be wirelessly transmitted. In some embodiments, the link 1228 may be a RJ45 connector through which Ethernet-based data passes, but in other embodiments it may be another type of connector through which Ethernet-based data may pass or may transmit a different type of data. As with the links 1212 and 1214, the link 1228 may be integrated into a PCA disposed inside of the hub 101 in some embodiments or it may be disposed on the rear panel 212 in other embodiments.

Further, the hub 101 includes a remote extender 1234. In general, the remote extender 1234 is configured to extend the range of USB communications by converting USB-based data to fiber optic-based data so that the data may be transported over long distances (e.g. up to 500 meters). In the illustrated embodiment, the USB connectors 240 are communicatively coupled to the remote extender 1234, which is in turn, coupled to the MPO link 1208. As such, the processing system 120 may communicate with USB-based devices such an input device 1236 (e.g. joystick, mouse, keyboard, touchpad etc) even if the hub 101 is located hundreds of meters from the workstation. Additionally, the FLIUVS PIM connector 232 is communicatively coupled to the remote extender 1234, and thus may pass USB-based data to the processing system 120 via the hub 101. Further, as shown in FIG. 12, the FLIVUS foot switch connector 234 and the ECG device connector 238 are communicatively coupled to the FLIVUS connector 232 so that signals from a FLIVUS footswitch 1238 and the ECG device 116 may be used to coordinate data collection by a FLIVUS PIM 1240 coupled to the connector 232.

The hub 101 includes a power distribution module 1242 configured to distribute power to medical sensing-related tools connected to the hub. In the illustrated embodiment, the power distribution module 1242 is a hardware-based module. However, in other embodiments, the module 1242 may be a combination of hardware and software, in which software controls power flow through the hardware. In the illustrated embodiment, a link 1244 electrically couples the power distribution module 1242 to a 48 volt DC medical-grade power supply in the workstation 120. In other embodiments, however, the power distribution module 1242 may draw power from another power source such as a wall receptacle. The power distribution module 1242 converts the power provided by the processing system 120 into a plurality of power amounts (i.e. levels), which are appropriately routed to various connectors in the hub 101. For instance, the power distribution module 1242 is electrically coupled to the first and second fiber optic connectors 224 and 226 and provides them with 48 volts DC. The power distribution module 1242 is also electrically coupled to the OCT PIM connector 228, the bedside control surface connector 230, the auxiliary power connector 236, and the FLIVUS PIM connector 232 and respectively provides them with, 48 volts DC, 12 volts DC, 24 volts DC, and 48 volts DC. Additionally, the power distribution module 1242 provides 12 volts DC to the wireless module and 5 volts DC to the remote extender 1234 which, in turn, supplies the USB connectors 240 with 5 volts DC. In alternative embodiments, the power amounts distributed to the connectors may vary. In further embodiments, the power distribution module 1242 may be operable to determine the amount of power required by medical sensing-related tool connected to a connector on the hub 101 and dynamically supply the correct amount of power. In yet further embodiments, the hub 101 may include a controller to interrogate newly-connected medical sensing tools to determine operational attributes such as voltage requirements. U.S. Patent Application No. 61/473,625, entitled "MEDICAL SENSING COMMUNICATION SYSTEM AND METHOD", discloses a medical sensing communication system that includes a controller and power supply unit that are operable to dynamically supply different medical sensing tools with different amounts of power based on their needs and is hereby incorporated by reference in its entirety. In the illustrated embodiment, the processing system 120 provides the hub 101 with 48 volts DC via a power cable 1246 that is coupled to the link 1244. In some embodiments, the link 1244 may be coupled to a PCA disposed inside of the hub 101 near the aperture 214, but, in other embodiments, the link 1244 may be disposed on the rear panel 212 for easy access. Additionally, as shown in FIG. 12, the hub 101 may be electrically coupled to a ground line 1248 via a cable 1250. Although not shown for purposes of clarity, the ground is distributed to the various connectors on the front panel of the hub 101 that draw power from the power distribution module 1242 so that the connectors may pass along the ground to the connected tools.

As mentioned above, the front interface panel 210 (FIG. 2A) and the connectors 220, 222, 224, 226, 228, 230, 232, 234, 236, 238, 240, and 242 described above may together be considered a forward interface assembly. Further, the rear interface panel 212 (FIG. 3) and the links 1200, 1204, 1208, 1212, 1214, 1220, 1224, 1228, and 1244 may together considered a rear interface assembly. Thus, as described above, in some embodiments the rear interface assembly may include internal portions of the hub 101 (e.g. when the links are integrated into a PCA disposed inside of the hub).

With reference now to FIGS. 1, 3 and 12, the rear interface assembly of the hub 101 may be assembled in the following manner. First, after cables 1202, 1206, 1216, 1218, 1246, 1222, 1210, 1232, 1226, and 1250 have been installed in trench 126 such that they enter the catheter lab 102 through trench entry port 128, they may be threaded through a coupler, the flexible hose 124, and another coupler such as straight coupler 262. With the rear panel 212 and/or housing removed from the hub 101, the cables may then be threaded through the aperture 214 in the rear panel 212 and coupled to their respective links inside of the hub 101. For instance, the cables 1216 and 1218 may be coupled to the links 1212 and 1214, which, in some embodiments, may be integrated into a PCA disposed within the hub 101. Once every cable extending from the processing system 120 has been coupled to the hub 101, the rear panel 212 may be fixedly secured to the hub 101 with connectors such as screws. As noted above, when the rear panel 212 is coupled to the hub 101, the gasket 213 creates a fluid-resistant interface between the two. Next, the coupler 262 may be fixedly coupled around the aperture 214 in the rear panel 212 with connectors such as screws, and the flexible tube 124 may be fixedly secured to coupler 262 on its hub-end and to another coupler on its trench-end. Once assembly is complete, the cables connecting the processing system 120 to the hub 101 and their associated links inside of the hub are protected from damaging elements in the catheter lab such as fluids and impact. One of ordinary skill in the art would understand that the previous assembly scenario is simply one example and other scenarios using different elements and/or positioning may be implemented.

Figure 13:
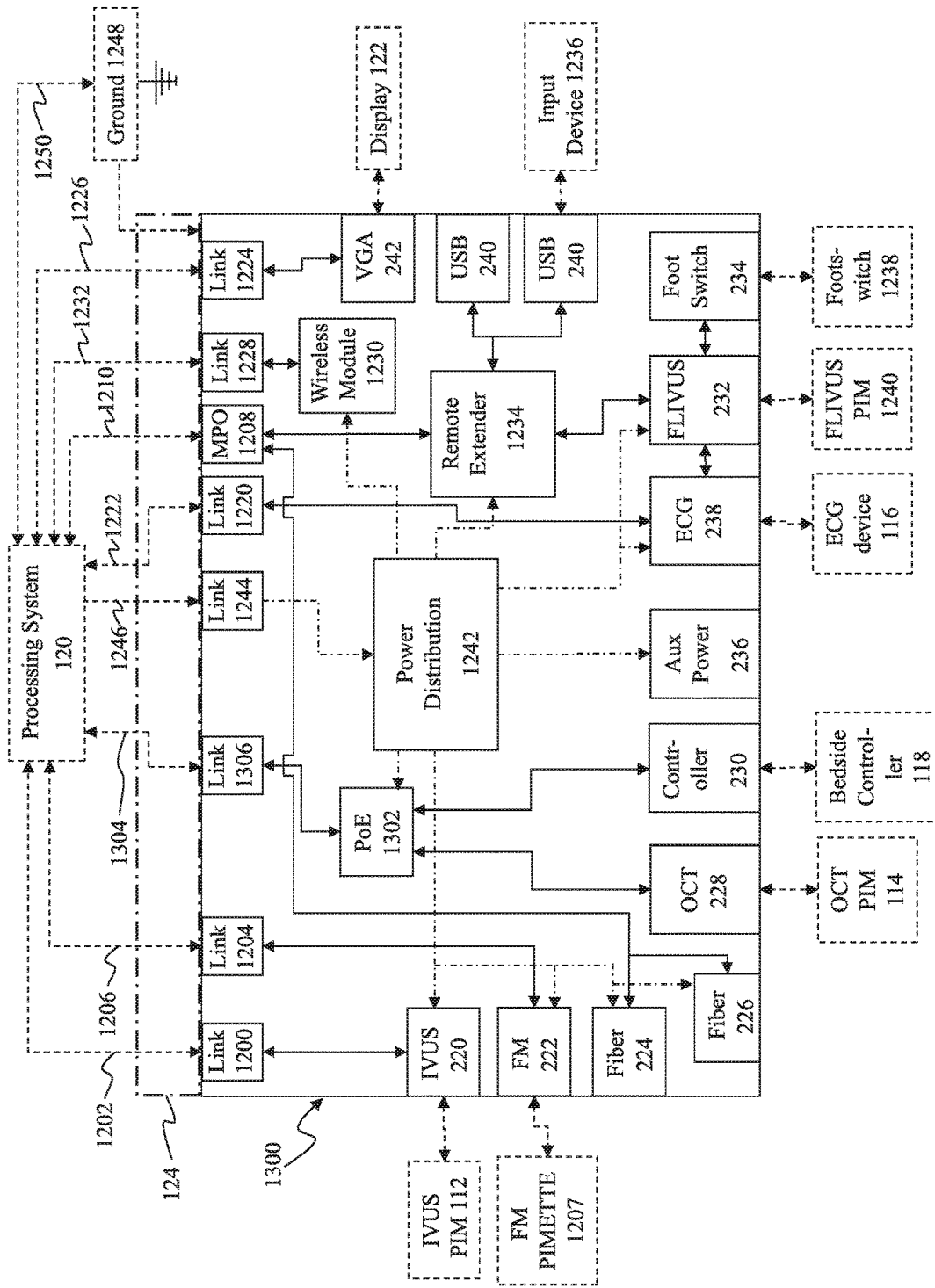
FIG. 13 is a functional block diagram of a further embodiment of a powered medical communication hub.

FIG. 13 is a functional block diagram of a powered medical communication hub 1300 according to another embodiment of the present invention. The hub 1300 is similar to the hub 101 shown in FIG. 12 but differs in several aspects as described below. Specifically, the hub 1300 includes a Power-over-Ethernet (PoE) module 1302 communicatively interposed between the processing system 120 and the OCT PIM connector 228 and the bedside control surface connector 230. A shown in FIG. 13, a single Cat5e cable 1304 (or other Ethernet-compatible communication medium) may extend from the processing system 120 to an Ethernet-based link 1306 in the hub 1300. The link 1306, in turn, communicatively couples to the PoE module 1302, where packetized data is routed to the appropriate connector. Further, the PoE module 1302 draws power (e.g. 48 volts DC) from the power distribution module 1242 and passes it to downstream Ethernet-based devices via the connectors 228 and 230. The downstream devices may, in turn, utilize the power as needed. In alternative embodiments, the PoE module 1302 may draw power from the processing system 120 via link 1306 in addition to or instead of drawing power from the power distribution system 1242. Further, in the embodiment of FIG. 12, the IVUS PIM connector 220 and FM tool connector 222 draw power directly from their respective links 1200 and 1204, however, in the embodiment of FIG. 13, these connectors may draw power directly from the power distribution module 1242. Additionally, in hub 1300, the ECG connector 238 may draw power from the power distribution module 1242 as well.

Figure 14:
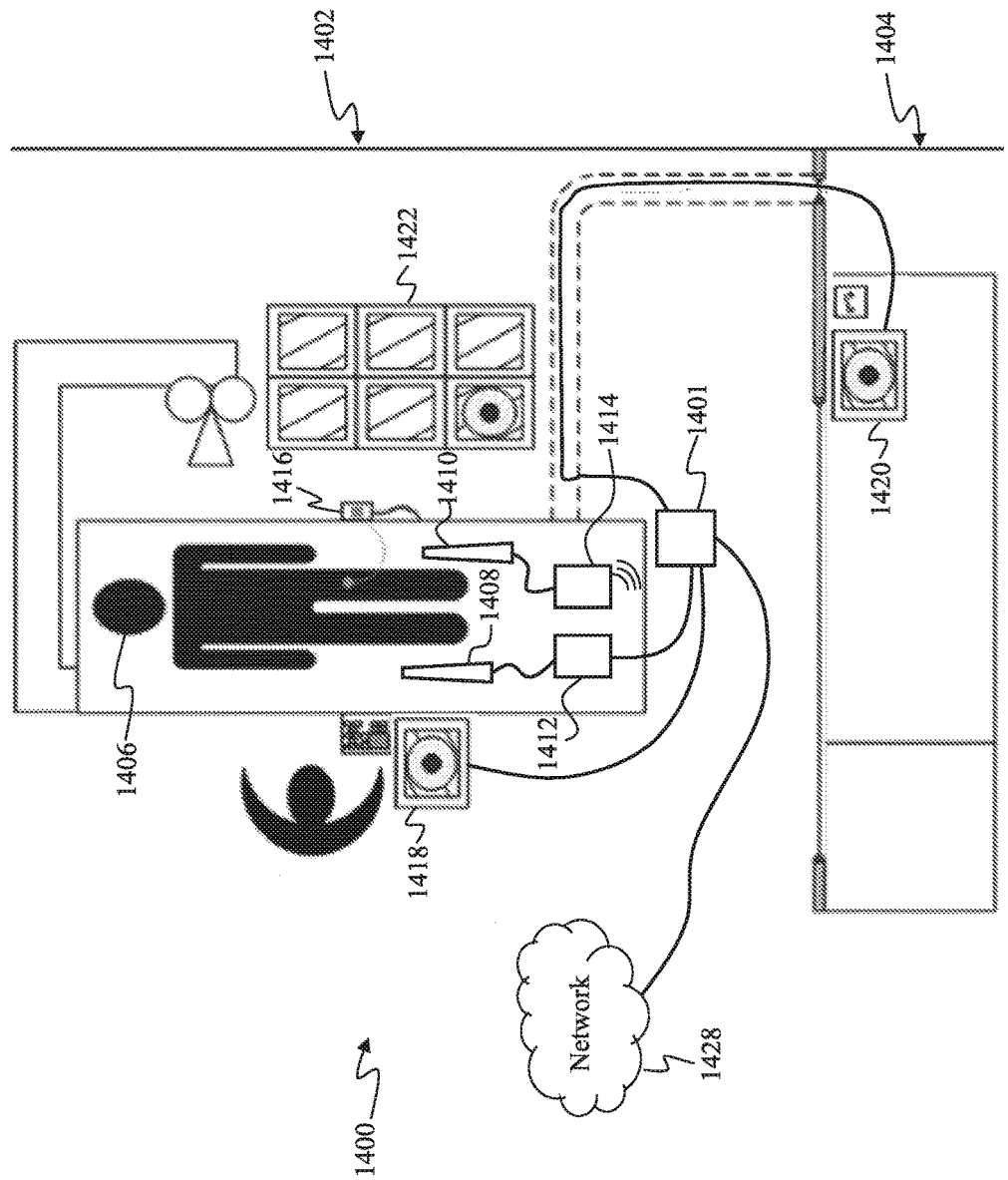
FIG. 14 is a schematic drawing depicting a medical sensing communication system including a bedside utility box according to one embodiment of the present disclosure.

FIG. 14 is a schematic drawing depicting a medical sensing communication system 1400 including a bedside utility box (BUB) 1401. The medical sensing communication system 1400 is a network-connected, data collection solution for multiple modality medical sensing. Generally, in the system 1400, the BUB 1401 is a central hub that interconnects a plurality of medical sensing-related tools and facilitates communication between the tools and a data network. In one embodiment, the communication system 1400 may be utilized to collect data from medical sensing devices and transmit it to remote computing resources, where it is processed and returned. U.S. Provisional Patent Application No. 61/473,570, entitled "MULTI-MODALITY MEDICAL SENSING SYSTEM AND METHOD" and filed on Apr. 8, 2011, discloses a computing resource capable of processing multi-modality medical sensing data and is hereby incorporated by reference in its entirety.

In the illustrated embodiment, the medical sensing communication system 1400 is deployed in a catheter lab 1402 having a control room 1404. The catheter lab 1402 includes a sterile field but its associated control room 1404 may or may not be sterile depending on the requirements of a procedure and/or health care facility. The catheter lab and control room may be used to perform on a patient any number of medical sensing procedures such as angiography, intravascular ultrasound (IVUS), virtual histology (VH), forward looking IVUS (FL-IVUS), intravascular photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intravascular palpography, transesophageal ultrasound, or any other medical sensing modalities known in the art. For example, in catheter lab 1402 a patient 1406 may be undergoing a multi-modality procedure, in which IVUS data will be collected with an IVUS catheter 1408 and OCT data will be collected with an OCT catheter 1410. The IVUS catheter 1408 may include one or more sensors such as a phased-array transducer. In some embodiments, the IVUS catheter 1408 may be capable of multi-modality sensing such as IVUS and IVPA sensing. The OCT catheter 1410 may include one or more optical sensors.

The communication system 1400 includes a number of interconnected medical sensing-related tools in the catheter lab 1402 and control room 1404 to facilitate this multi-modality workflow procedure, including an IVUS patient isolation module (PIM) 1412, an OCT PIM 1414, an electrocardiogram (ECG) device 1416, a bedside control surface 1418, a control room control surface 1420, and a boom display 1422. The BUB 1401 in the catheter lab 1402 interconnects these medical sensing-related tools and communicatively couples them to a data network 1428. That is, the BUB 1401 is a central hub through which the tools in the catheter lab 1402 and control room 1404 connect to the data network 1428. In the illustrated embodiment, the data network 1428 is TCP/IP-based local area network (LAN), however in other embodiments, it may utilize a different protocol such as Synchronous Optical Networking (SONET), or may be a wide area network (WAN). Further, in another embodiment, the data network 1428 may be a data bus network, such as a Universal Serial Bus (USB) network, for connecting BUB 1401 to a host controller with computing resources. The BUB 1401 will be described in greater detail in association with FIGS. 14-17.

In the illustrated embodiment of FIG. 14, the IVUS catheter 1408, PIM 1412, and the BUB 1401 together may be considered a patient communication system that is operable to receive medical sensing data collected from the patient 1406 by the IVUS catheter 1408 and to transmit the received data onto the data network 1428. As shown, the BUB 1401 is communicatively coupled to the IVUS patient isolation module (PIM) 1412 via a wired connection such as a standard copper link or a fiber optic link, and the IVUS PIM is, in turn, coupled to the IVUS catheter 1408 via a similar wired connection. In alternative embodiments, however, the BUB-PIM connection and/or the PIM-catheter connection may be wired or wireless. In one embodiment, the PIM 1412 includes an analog to digital (A/D) converter and transmits digital data to the BUB 1401, however, in other embodiments the PIM transmits analog data to the BUB. Further, in some embodiments, the PIM 1412 and BUB 1401 communicate with a standardized data transmission protocol, such as Synchronous Optical Networking (SONET). Further, the PIM 1412 provides power to data collection sensors disposed on the catheter 1408 via its connection to BUB 1401. Typically, different sensory instruments require different amounts of power, and thus their associated PIMs may draw different amounts of power from the BUB 1401. As discussed later, the BUB 1401 is operable to dynamically provide the appropriate amount of power to IVUS PIM 1412 via the wired connection.

Further, the OCT catheter 1410 and PIM 1414 may also be considered a part of the patient communication system that includes PIM 1412 and BUB 1401. With the OCT catheter 1410 and PIM 1414 the patient communication system is further operable to receive medical sensing data collected by the OCT catheter 1410 and transmit the received data onto the data network 1428. In the illustrated embodiment, the OCT PIM 1414 is communicatively coupled to BUB 1401 via a wireless connection, but in alternative embodiments, may be communicatively coupled via a wired connection. In one embodiment, the PIM 1414 includes an A/D converter and transmits digital data to the BUB 1401, however, in other embodiments the PIM transmits analog data to the BUB. Further, in some embodiments, the PIM 1414 and BUB 1401 communicate with a standardized data transmission protocol, such as SONET. In some embodiments, the PIM 1414 may include a battery to power catheter 1410, may draw power from a wired power connection, or may be wirelessly powered.

For convenience purposes, the PIMs 1412 and 1414 may hang from the patient table or may be placed in another location near the patient. Although two PIMs are depicted as communicatively coupled to the BUB 1401, additional PIMs associated with different medical sensing modalities may be connected to BUB 1401. Any such additional PIMs may communicate with the BUB 1401 concurrently with the PIMs 1412 and 1414. Still further, a single PIM may support multiple modalities, such as IVUS and IVPA. Additionally, in some embodiments, such as those in which patient data is collected using angiography, one of the illustrated PIMs may be replaced with a C-arm. In such embodiments, the C-arm may act as the power and data intermediary between the angiography sensors and the network 1428. Still further, in another embodiment, the medical sensing communication system 1400 may include an adapter device to serve as an intermediary between a third-party system such as an angiography system and the BUB 1401. Such an adaptor device may transform data in a proprietary third-party format into a format usable by the system 1400. U.S. Patent Application Publication No. US 2007/0232933,entitled "Component-Based Catheter Lab Intravascular Ultrasound System," discloses a component-based IVUS system that includes a PIM and is hereby incorporated by reference in its entirety.

As mentioned above, the ECG device 1416 is also communicatively coupled to BUB 1401 via a wired or wireless connection. The ECG device 1416 is operable to transmit electrocardiogram signals from patient 1406 to the BUB 1401. In some embodiments, the BUB 1401 may be operable to synchronize data collection with the catheters 1408 and 1410 using the ECG signals from the ECG 1416.

The bedside control surface 1418 is also communicatively coupled to the BUB 1401 and provides user control of the particular medical sensing modality (or modalities) being used to diagnose the patient 1406. In the current embodiment, the bedside control surface 1418 is a touch screen that provides user controls and diagnostic images on a single surface. In alternative embodiments, however, the bedside control surface 1418 may include both a non-interactive display and separate controls such as physical buttons and/or a joystick. In the illustrated embodiment, the bedside control surface 1418 and BUB 1401 communicate over a wired connection such as a standard copper link or a fiber optic link but, alternatively, the control surface 1418 and BUB 1401 may communicate wirelessly. Further, in some embodiments, the bedside control surface 1418 may also be communicatively coupled directly to one or both of PIMs 1412 and 1414. The bedside control surface 1418 includes an integrated processing unit to drive a graphical user interface (GUI)-based workflow presented on the touch screen. In an exemplary embodiment, the particular GUI-based workflow presented by the bedside control surface 1418 depends on the medical sensing modality being used to diagnose the patient 1406. To this end, the bedside control surface 1418 is capable of displaying multiple GUI-based workflows, each corresponding to a particular sensor or imaging modality or simultaneous combination thereof. The bedside control surface 1418 is further operable to display co-registration GUI-based workflows, for example, to integrate sensing data collected by catheters 1408 and 1410. An API-based software framework executing on the bedside control surface 1418 manages the multiple workflows. U.S.

Patent Application No. 61/473,591, entitled "Distributed Medical Sensing System and Method" and filed on Apr. 8, 2011, discloses a bedside control surface that executes GUI-based workflows using a software framework and is hereby incorporated by reference in its entirety.

The control room control surface 1420 in the control room 1404 is also communicatively coupled to the BUB 1401 and, as shown in FIG. 14, is adjacent to catheter lab 1402. In the illustrated embodiment, the control room control surface 1420 and BUB 1401 communicate over a wired connection such as a standard copper link or a fiber optic link but, alternatively, the control surface 1420 and BUB 1401 may wirelessly communicate. In the current embodiment, the control room control surface 1420 is similar to the bedside control surface 1418 in that it includes a touch screen, integrated processing unit, and multitude of GUI-based workflows corresponding to different medical sensing modalities. During a procedure, however, the control room control surface 1420 may be used to carry out a different aspect of the procedure's workflow than the bedside control surface 1418. In alternative embodiments, the control room control surface 1420 may include a non-interactive display and standalone controls such as a mouse and keyboard. Further, the processing unit of the control room control surface 1420 may be more powerful than the processing unit of the bedside control surface 1418.

The system 1400 further includes the boom display 1422. The boom display 1422 may include an array of monitors, each capable of displaying different information associated with a medical sensing procedure. For example, during an IVUS procedure, one monitor in the boom display 1422 may display a tomographic view and one monitor may display a sagittal view. In an embodiment as described in FIG. 17, the boom display 1422 may be coupled directly to and driven by the BUB 1401. In other embodiments, the boom display may also be operable to receive image data from the bedside control surface 1418 or the control room control surface 1420.

Figure 15:
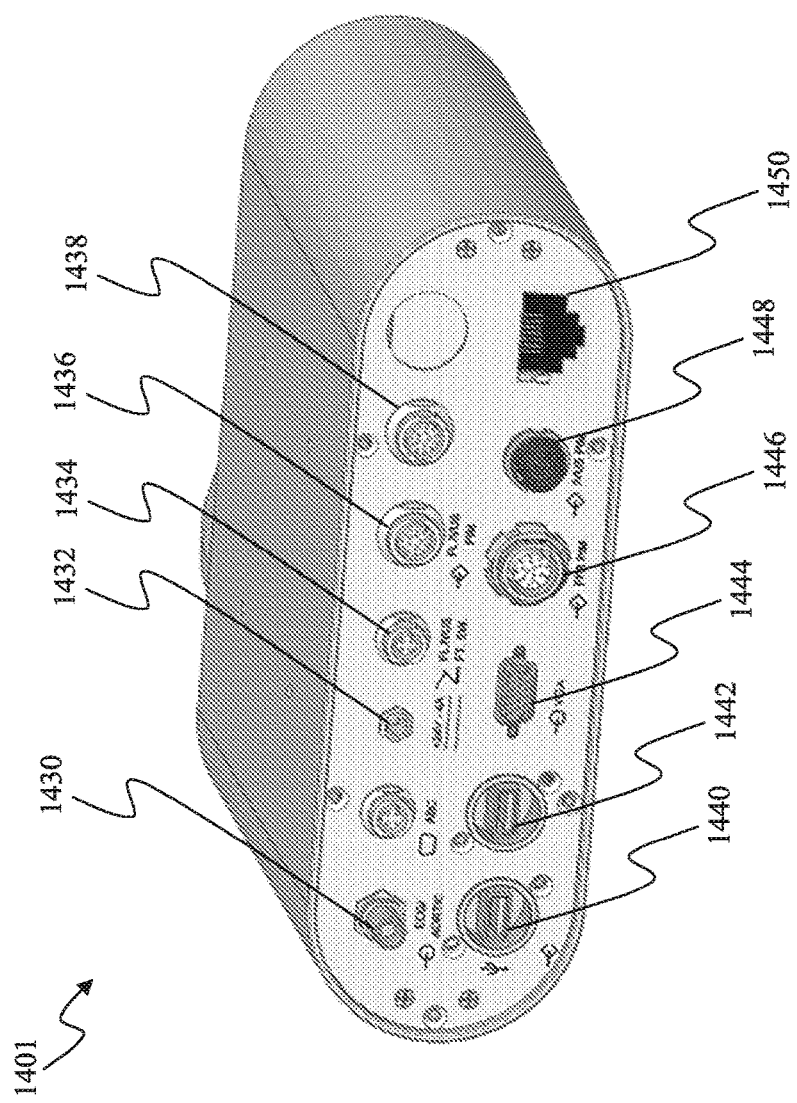
FIG. 15 is a diagrammatic perspective view of the bedside utility box of FIG. 1.

With reference now to FIG. 15, illustrated is an aspect of the medical sensing communication system 1400. Specifically, FIG. 15 is a diagrammatic perspective view of the bedside utility box (BUB) 1401 of FIG. 14. As mentioned above, the BUB 1401 is a hub through which the medical sensing-related tools communicate with data network 1428. In general, the BUB 1401 is operable to collect medical sensing data from connected medical sensing devices such as the IVUS PIM 1412 and OCT PIM 1414 and send it to remote computing resources to be processed. Once processed, the medical sensing data may be returned to the BUB 1401, where it is routed to the control surfaces 1418 and 1420 to be displayed and analyzed by clinicians.

The BUB 1401 includes a number of sockets to which the medical sensing-related tools connect. In the illustrated embodiment, the BUB 1401 includes an ECG socket 1430, an auxiliary power socket 1432, a FLIVUS foot switch socket 1434, a FLIVUS PIM socket 1436, an OCT PIM socket 1438, two USB sockets 1440 and 1442, a display socket 1444, a FFR PIM socket 1446, a IVUS PIM socket 1448, and a network communication socket 1450. Referring to FIGS. 14 and 15, the ECG device 1416 may couple to the ECG socket 1430, the IVUS PIM 1412 may couple to the IVUS PIM socket 1448, the bedside controller 1418 may couple to the USB socket 1440, and the control room control surface may couple to the USB socket 1442. The USB sockets 1440 and 1442 to which the control surfaces 1418 and 1420 connect may alternatively be replaced with other short-distance high-speed ports such as FireWire ports or Thunderbolt ports. Further, in some embodiments, the boom display 1422 may be coupled to the display socket 1444, which, in the current embodiment, is a VGA port, but may alternatively be a DVI port, S-video port, DisplayPort port, HDMI port, or other type of video display port. Additionally, the BUB 1401 may communicate with the network 1428 through the network communication socket 1450. In the illustrated embodiment, the network communication socket 1450 is an Ethernet port, but alternatively, it may be another type of network communication port such as a fiber optic port. Or, if the network 1428 is a data bus network, the network communication socket 1450 may be a USB port, a InfiniBand port, a HyperTransport port, a Thunderbolt port, FireWire port, or other data bus port. In the illustrated embodiment, the sockets of BUB 1401 providing connectivity to medical sensing-related tools are dedicated to a specific medical sensing modality and thus conform to a number of different form factors. However, in alternative embodiments, the sockets may be substantially similar (i.e. are standardized). Further, although the BUB 1401 includes certain sockets for specific medical sensing-related tools, in other embodiments, it may include additional and/or different sockets to connect medical sensing devices, controllers, and displays.

Figure 16:
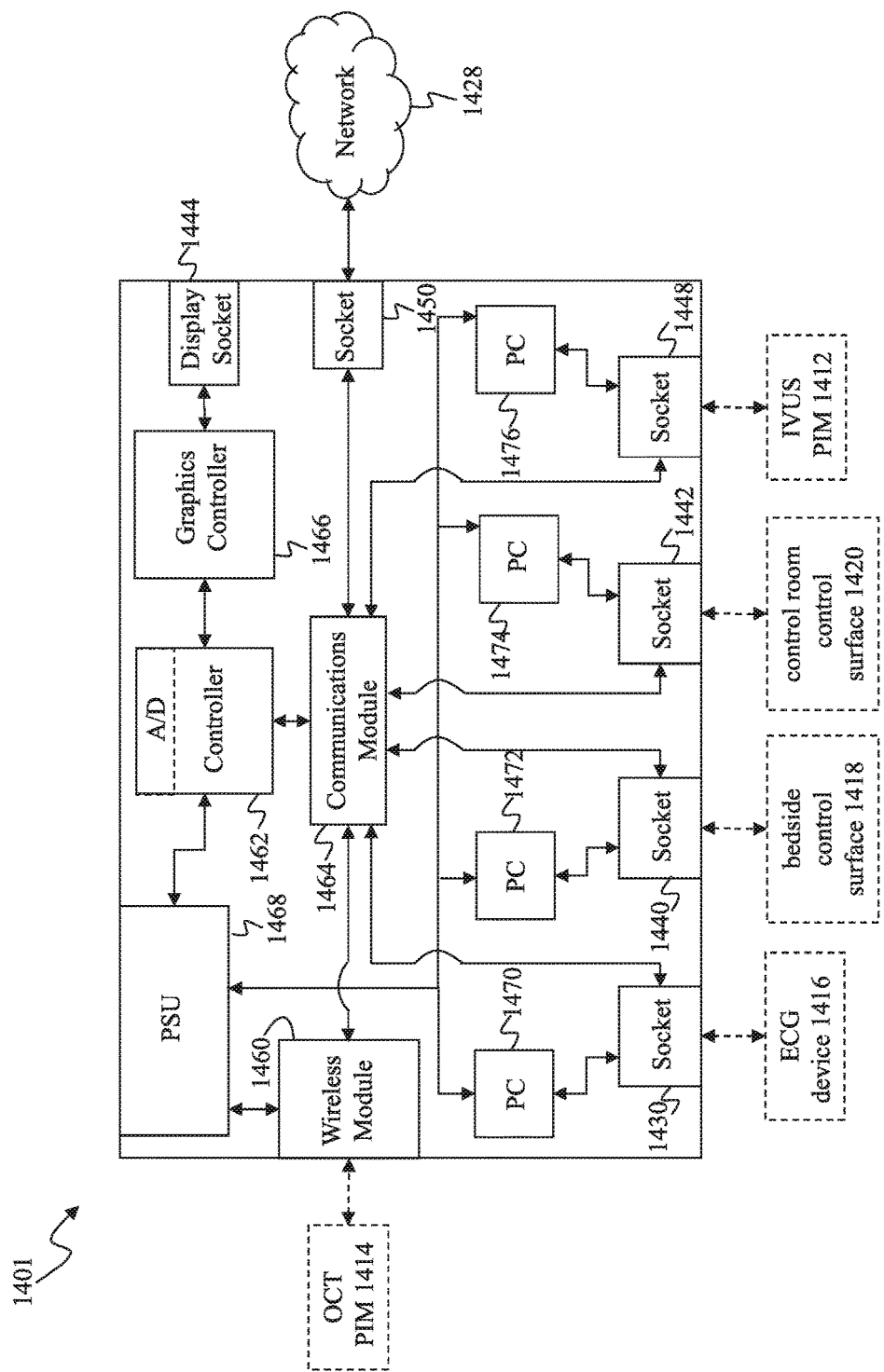
FIG. 16 is a functional block diagram of an embodiment of a bedside utility box.

FIG. 16 is a functional block diagram of an embodiment of a bedside utility box (BUB). As described in FIG. 15, the BUB 1401 may include the ECG socket 1430, USB socket 1440 and 1442, and the IVUS PIM socket 1448, to which the ECG device 1416, bedside control surface 1418, control room control surface 1420, and IVUS PIM 1412 respectively connect. The BUB 1401 also includes the display socket 1444 and network communication socket 1450, to which the boom display 1422 and network 1428 respectively connect. For purposes of clarity, the other sockets of BUB 1401 illustrated in FIG. 15 have been omitted from the functional block diagram of FIG. 16. The BUB 1401 further includes a wireless communication module 1460 operable to communicate with medical sensing-related tools in close proximity to the BUB, such as the OCT PIM 1414. In one embodiment, the wireless communication module 1460 may be a wireless personal area network (WPAN) communication module such as an Ultra-wide band (UWB) module, a wireless FireWire module, or wireless USB module or some other high-speed wireless module.

The BUB 1401 further includes a controller 1462 and a communication module 1464. In some embodiments, the controller 1462 may be a low-power microcontroller with integrated memory and peripherals (i.e. a system-on-a-chip). However, in other embodiments, the controller may be a general-purpose, central processing unit (CPU). The controller 1462 (i.e. control module) is operable, among other things, to route data from the sockets 1430, 1440, 1442, 1448 and the wireless communication module 1460 to the communication module 1464, where it may be transmitted to the network 1428 via socket 1450. In the current embodiment, the controller 1462 includes an analog to digital (A/D) converter which the controller may selectively utilize based on whether data incoming from a connected PIM is in analog or digital form. For example, the controller 1462 may convert analog data from a PIM to digital data before it is routed to the communication module 1464. Additionally, in some embodiments, the controller 1462 may be operable to associate identifying information with the medical sensing data as it is routed to the communications module 1464. More specifically, the controller 1462 may create a plurality of digital messages from the incoming analog or digital data stream, where each message contains a portion of the digitized medical sensing data and a header. The aforementioned U.S. Patent Application No. 61/473,591, entitled "Distributed Medical Sensing System and Method," discloses creating messages that associate identifying information with medical sensing data in more detail.

Further, in the event that multiple medical sensing devices are coupled to the BUB 1401, as illustrated in FIG. 16, the controller 1462 may be operable to facilitate time synchronization among the devices for co-registration purposes. For instance, in one embodiment, the controller 1462 may be operable to serve as a master time server for the PIMs 1412 and 1414 using a network-based time synchronization protocol such as the Precision Time Protocol (PTP) or the Network Time Protocol (NTP). In another embodiment, the controller 1462 may be operable to assign a common timestamp to data as it arrives into the BUB 1401 from a plurality of medical sensing devices. Further, in another embodiment, the controller 1462 may communicate with connected medical sensing devices using a synchronous protocol such as Synchronous Optical Networking (SONET), and may assign timestamps to incoming medical sensing data based on the multiplexed communication. Still further, in other embodiments, the BUB 1401 may include a dedicated real-time clock to synchronize sampling by connected medical sensing devices. In such an embodiment, the real-time clock may distribute a synchronization signal to connected sensing devices and also the controller 1462 which may act as a co-registration processor. In some embodiments, the real-time clock may be integrated into the controller 1462. The aforementioned U.S. Patent Application No. 61/473,591, entitled "Distributed Medical Sensing System and Method," discloses temporally synchronizing medical sensing data collection in more detail.

Further, in some embodiments, the controller 1462 may be operable to modify the medical data received from the medical sensing devices as it is routed to the communication module 1464. For example, in some embodiments, the controller 1462 may compress the data before it is transmitted over the network 1428. In this manner, large data sets produced by imaging modalities such as OCT may be more efficiently moved over the network 1428. In some embodiments, the controller 1462 may also be operable to filter incoming sensing data in some manner.

The communication module 164 in the BUB 1401 is a high-speed communication module operable to transmit data received from the medical sensing-related tools connected to the BUB 1401 and the network 1428. In embodiments in which the network 1428 is packet-based, the communication module 1464 is operable to packetize medical sensing data routed by (and possibly digitized by) the controller 1462, address the resulting packets, and the send the packets out over the network 1428. In the embodiments in which the controller 1462 segments incoming sensing data into messages, the communication module 1464 may encapsulate the messages into TCP/IP packets for transmission over the network 1428. In the illustrated embodiment, the communication module 1440 is an Ethernet-based communication module, however, in other embodiments the communications module may be a InfiniBand switched fabric communications module, HyperTransport communication module, a fiber optic link module, a USB controller, a Thunderbird controller, a FireWire controller, a high-speed wireless module or some other high-speed communication module known in the art.

The BUB 1401 further includes a graphics controller 1466 operable to output images to the display socket 1444. In the illustrated embodiment, the graphics controller 1466 is a graphics processing unit (GPU) independent of the controller 1462, but, in other embodiments, it may be integrated into the controller 1462 or be a plug-in, off-the-shelf component. Further, in some embodiments, the BUB 1401 may include a plurality of display sockets, where the graphics controller 1466 is capable outputting distinct video signals to each. The graphics controller 1466 gives the BUB 1401 the capability to independently output images representative of medical sensing data received from the connected medical sensing devices. In some embodiments, this capability may be utilized to reduce network bandwidth requirements. For example, data associated with a medical sensing modality that requires minimal processing (e.g. FFR) may be processed by controller 1462 and immediately output to a display via graphics controller 1466, thereby eliminating the need to send the data over the network 1428 to be processed. Further, to mitigate against lost connectivity with network 1428 during a catheterization procedure, the graphics controller 1466 may be used to perform some rudimentary image processing of incoming medical sensing data. For example, if during an OCT procedure in which the BUB 1401 is receiving OCT data from OCT PIM 1414, the computing resources on network 1428 become unavailable, the controller 1462 and graphics controller 1466 may be operable to perform some minimal image processing on the OCT data and output rudimentary OCT images to the display boom 1422. Further, in some embodiments, the BUB 1401, upon receiving medical sensing data, may render basic image data with graphics controller 1466 and simultaneously transmit an unprocessed version of the medical data to computing resources on network 1426 for more advanced processing and storage. A software framework executing on the controller 1462 in the BUB 1401 manages the routing, analog to digital conversion, and image processing of incoming medical sensing data. This software framework will be discussed in greater detail in association with FIG. 17.

The BUB 1401 further includes a medical-grade power supply unit (PSU) 1468. The PSU 1468 provides power to the controller 1462, wireless module 1460, and the medical sensing-related tools (e.g. medical sensing devices, control surfaces) connected to the sockets 1430, 1440, 1442, and 1448. As mentioned above, different connected tools may have different power requirements. For example, a phased-array catheter for use in IVUS procedures may require more power than a pressure sensor mounted on the distal end of a guide wire for use in a FFR procedure. Thus, in the current embodiment, the PSU 1468 is a multi-stage power supply that includes an isolating transformer to step down an input AC voltage and a plurality of switching power converters (PC) 1470, 1472, 1474, 1476 to dynamically output a desired voltage at a specific socket. For example, the PSU 1468 may step down a 120V AC supply to an intermediate DC voltage and then each power converter (i.e. power module) may convert the intermediate voltage to one of a plurality of DC voltages such as 48V, 24V, 12V, 5V, and 3.3V. The specific voltage output to each socket dynamically depends on the specific power requirements of the medical sensing-related tool connected. In one embodiment, the PCs 1470, 1472, 1474, 1476 may be physically integrated into the PSU 1468. In other embodiments, the PSU 1468 may be a different type of power supply known in the art and power conversion and distribution may be done by other methods known by those of ordinary skill in the art.

Additionally, upon connection of a medical sensing-related device to one of the sockets 1430, 1440, 1442, and 1448, the controller 1462 is operable to automatically interrogate the tool to determine connection attributes such as voltage and communication protocol. In the current embodiment, the controller 1462 utilizes a low-voltage (e.g. 5V) TTL logic initialization process to communicate with a newly connected medical sensing tool. In alternative embodiments, however, a different type of initialization process may be used. After the initialization process is complete, the controller 1462 is operable to dynamically set the voltage output to the tool and, in some embodiments, the protocol with which the tool communicates with the BUB 1401.

Note that the functional block diagram shown in FIG. 16 has been simplified for the sake of clarity. A person of ordinary skill in the art would understand that elements of the BUB 1401 may be rearranged or combined and that additional elements may be added without changing the functionality described herein. Further, a person of ordinary skill in the art understands that in the context of the current disclosure, a module may refer to a hardware module, a software module, or a combination software and hardware module.

Figure 17:
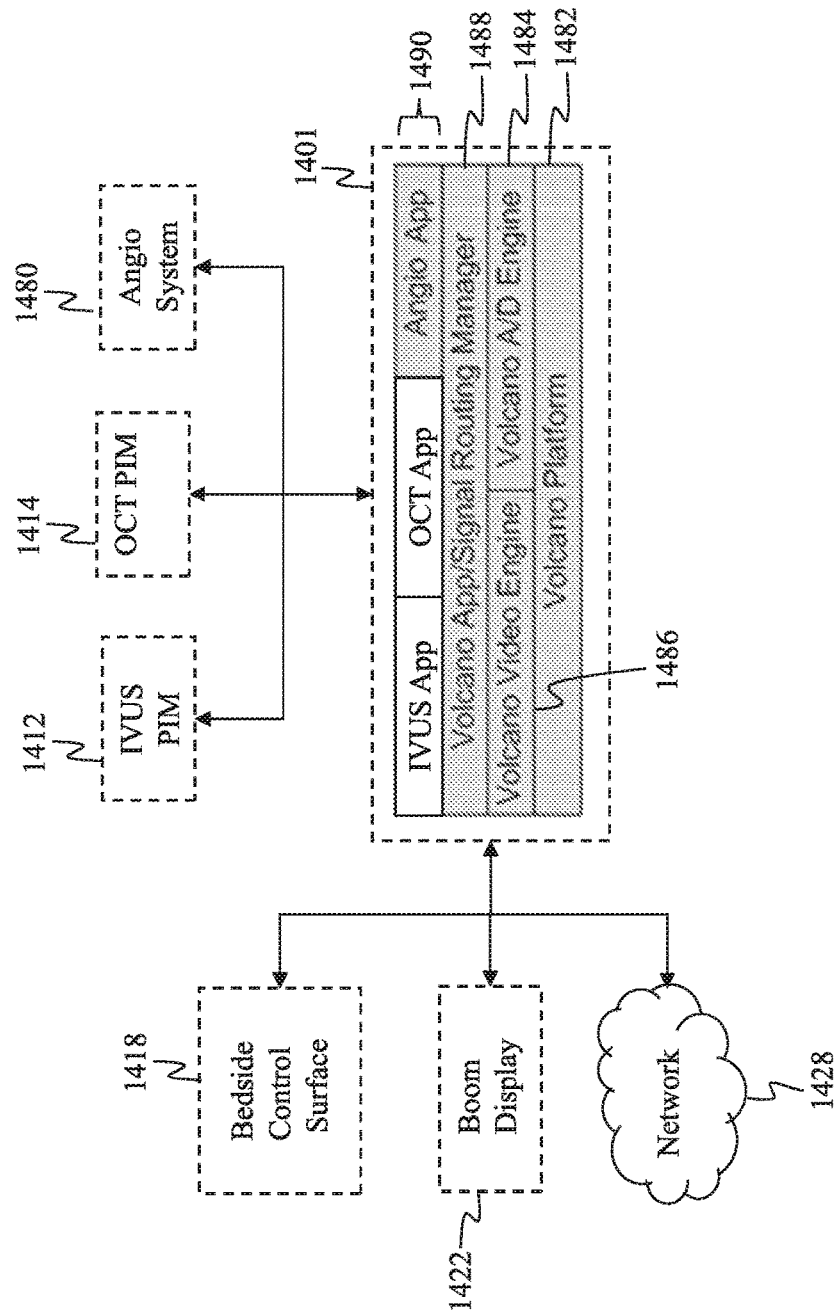
FIG. 17 is a functional block diagram of an aspect of the medical sensing communication system that includes a software framework executing on a bedside utility box.

With reference now to FIG. 17, illustrated is a functional block diagram of the software framework executing on the BUB 1401. More specifically, FIG. 17 illustrates one embodiment of the medical sensing communication system 1400 in which the IVUS PIM 1412, the OCT PIM 1414, an angiography system 1480, the bedside controller 1418, the boom display 1422, and data network 1428 are communicatively coupled to the BUB 1401. As mentioned above, the BUB 1401 includes a software framework to route, digitize, and process medical data received from connected medical sensing devices. The software framework includes a plurality of software layers that manage various aspects of the BUB 1401. For instance, an operating platform 1482 undergirds the software framework and provides the core functionality of the BUB 1401. For instance, the operating platform 1482 may manage power consumption and distribution of the BUB 1401 and may also manage network connectivity. Further, the software framework may include an analog to digital conversion engine 1484 operable to digitize analog data incoming from medical sensing devices, also may include a video engine 1486 operable to render images and video associated with medical sensing data. Additionally, the software framework includes a routing manager 1488 operable to control the routing of data between the medical sensing-related tools connected to BUB 1401 and the network 1428. In some embodiments, the routing manager may be operable to create a plurality of messages from digitized sensing data, where each message includes identifying information about the associated data.

Each of the software layers 1482, 1484, 1486, and 1488 additionally expose application programming interfaces (APIs) through which system resources may be accessed. The software framework in BUB 1401 includes a processing application layer 1490 in which processing applications associated with specific medical sensing modalities may execute. Utilizing the APIs exposed by the underlying software layers, the processing applications in the application layer 1490 may be operable to render video or other images (e.g. FFR signal traces) from the raw medical sensing data transmitted to the BUB 1401 by connected medical sensing devices. For example, if the BUB 1401 loses network connectivity with the network 1428, an IVUS processing application in the application layer 1490 may call video processing APIs exposed by the video engine 1486 to render IVUS video images for display on the boom display 1422. Further, in some embodiments, the application layer 1490 may include co-registration applications, in which medical sensing data from a plurality of medical sensing devices is co-registered and processed to produce co-registration images for display via the boom monitor 1422. For instance, a co-registration application may display an electrocardiogram (ECG) wave adjacent to IVUS imaging data. In an exemplary embodiment, additional processing applications may be added to the application layer 1490 to support new medical sensing modalities or co-registration techniques developed after the BUB 1401 has been deployed. Further, the API-based software framework allows the applications 1490 to be independent of the supporting software layers and thus written by third parties to control custom workflows.

Figure 18:
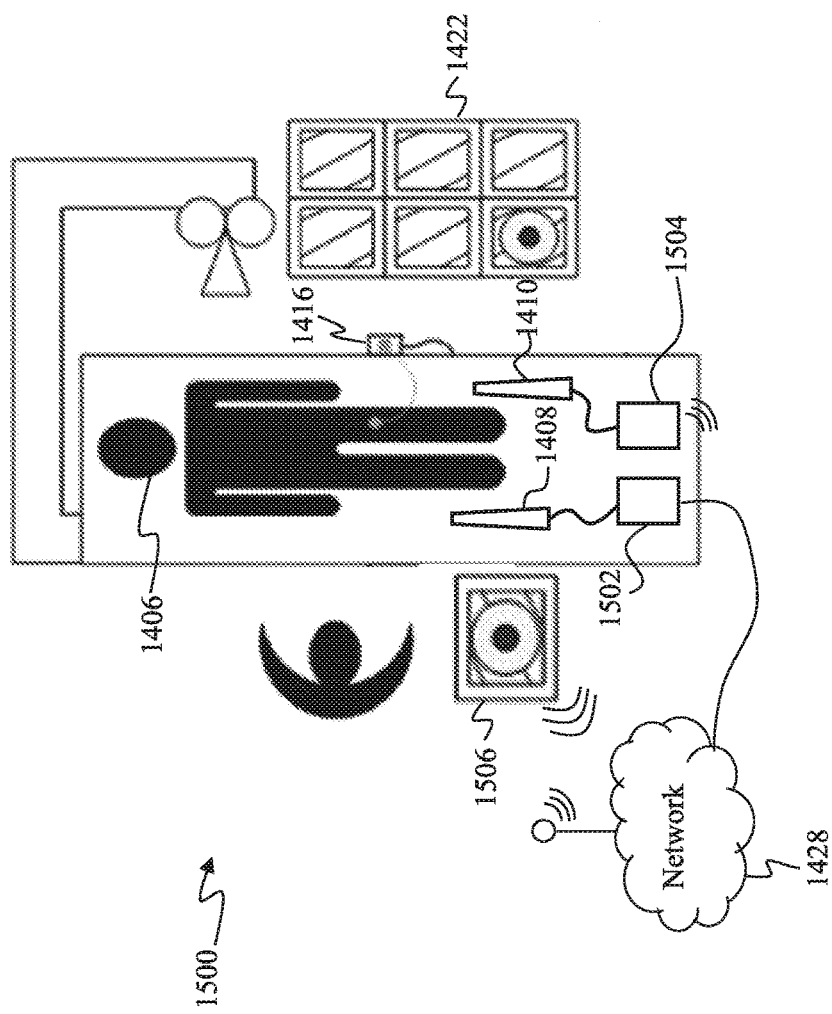
FIG. 18 is a schematic drawing depicting a medical sensing communication system according to another embodiment of the present disclosure.

Referring now to FIG. 18, shown is a schematic drawing depicting a medical sensing communication system 1500 according to another embodiment of the present disclosure. The medical sensing communication system 1500 is similar to the medical sensing communication system 1400 shown in FIG. 14 Like medical sensing communication system 1400, medical sensing communication system 1500 may be utilized to collect data from medical sensing devices in catheter room 1402 and transmit it to remote computing resources, where it is processed and returned. However, in system 1500, medical sensing devices collect and transmit medical sensing data to remote computing resources without the use of a bedside utility box (BUB).

In more detail, the patient 1406 may be undergoing a multi-modality procedure, in which IVUS data will be collected with the IVUS catheter 1408 and OCT data will be collected with the OCT catheter 1410. In the system 1500, the IVUS catheter 1408 is communicatively coupled to an IVUS PIM 1502. As mentioned above, the IVUS catheter 1408 may be capable of multi-modality sensing such as IVUS and IVPA, and PIM 1502 may likewise capable of receiving multi-mode sensor outputs. Without a BUB in system 1500, the IVUS PIM 1502 may itself be considered a patient communication system that is operable to receive medical sensing data collected by the IVUS catheter 1408 and transmit the received data onto the data network 1428. As such, the PIM 1502 is operable to perform similar functions that the PIM 1412 and BUB 1401 performed together in the patient communication system of FIG. 14. As shown, IVUS PIM 1502 is coupled to the IVUS catheter 1408 via a wired connection. In alternative embodiments, however, the PIM-catheter connection may be wired or wireless. In the illustrated embodiment, the PIM 1502 includes an analog to digital (A/D) converter and transmits digital data to the network 1428 via a wired connection. The IVUS PIM 202 will be described in greater detail in association with FIG. 19.

The medical sensing communication system 1500 further includes a OCT PIM 1504 configured to receive OCT data from the OCT catheter 1410. Like the IVUS PIM 1502, the OCT PIM 1504 may itself be considered a patient communication system in the absence of a BUB. The OCT PIM 1504 is operable to receive medical sensing data collected by the OCT catheter 1410 and transmit the received data onto the data network 1428. As shown, OCT PIM 1504 is coupled to the OCT catheter 1410 via a wired connection. In alternative embodiments, however, the PIM-catheter connection may be wired or wireless. In the illustrated embodiment, the PIM 1504 includes transmits digital data to the network 1428 via a wireless connection, such as an IEEE 802.11 Wi-Fi connection or another high-speed wireless connection.

The medical sensing communication system 1500 further includes a bedside control surface 1506. The bedside control surface 1506 may be similar to the bedside control surface 1418 of FIG. 14 in that it provides user control and displays images of the particular medical sensing modality (or modalities) being used to diagnose the patient 1406. However, in the current embodiment, the bedside control surface 1506 communicates with the network 1428 via a wireless connection, such as an IEEE 802.11 Wi-Fi connection or another high-speed wireless connection. The bedside control surface 1506 is operable to wirelessly transmit workflow control information to the PIMs 1502 and 1504 via the network 1428 and also receive medical sensing data from the PIMs that has been processed by remote computing resources on the network 1428. Because the bedside control surface 1506 is wireless, it may be moved to a control room, different catheter room, or even a doctor's office as needed. Although two PIMs are depicted as part of system 1500, additional PIMs associated with different medical sensing modalities may be integrated in to system 1500 and communicatively coupled to the network 1428 without the use of a BUB.

Figure 19:
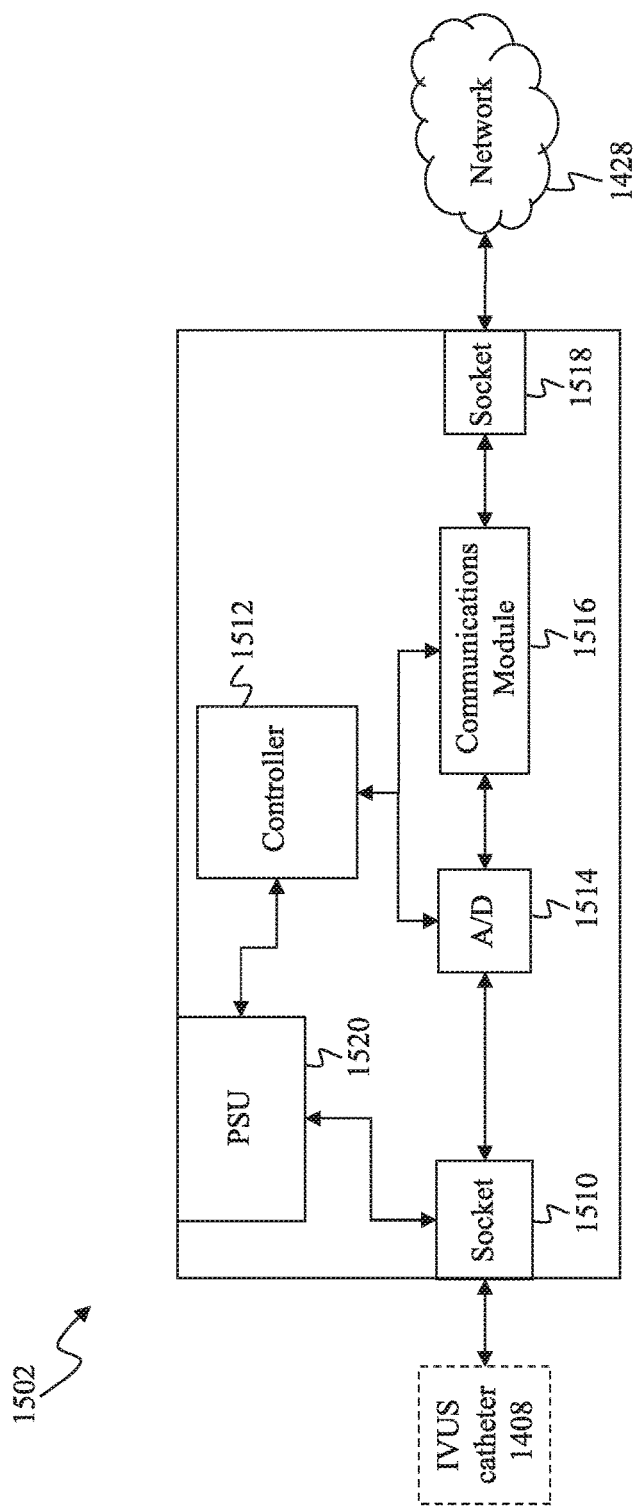
FIG. 19 is a functional block diagram of an exemplary embodiment of an aspect of the medical sensing communication system of FIG. 18, specifically, a patient isolation module.

FIG. 19 is a functional block diagram of an embodiment of the IVUS PIM 1502 of FIG. 18. As described in FIG. 18, the PIM 1502 is communicatively coupled to both the IVUS catheter 1408 and the network 1428 and is operable to route medical sensing data from the catheter to computing resources on the network. The PIM 1502 includes a socket 1510 to which the catheter 1408 connects. The socket 1510 may be a dedicated IVUS port or may be a standardized port such that any catheter with a matching standardized connector may connect to it. The PIM 202 further includes a controller 1512 operable to route data from the socket 1510 through an A/D converter 1514 and to a communications module 1516. In some embodiments, the controller 1512 may be similar to the low power controller 1462 in the BUB 1401 of FIG. 16. As the PIM 1502 is often placed near or on a patient during a procedure, it ideally gives off little or no heat in some embodiments. Alternatively, in some embodiments, the controller 1512 is coupled to a heat sink that disperses heat generated by the controller. Alternatively, the BUB 1401 may include active cooling elements to prevent heat buildup. Further, the controller 1512 is operable to digitize analog data received from the IVUS catheter 1408 with the A/D converter 1514. Although, the A/D converter is depicted as an independent hardware module, in some embodiments, the A/D converter may be a software module executing on the controller 1512. Additionally, in some embodiments, the data received from a catheter may already be digitized and thus controller 1512 may disable the A/D converter 1514.

Further, after incoming medical sensing data has been digitized, the controller 1512 routes it to the communication module 1516, which may be similar to the communication module 1464 in the BUB 1401 of FIG. 16. In some embodiments, the controller 1512 may be operable to associate identifying information with the medical sensing data as it is routed to the communications module 1516. More specifically, the controller 1512 may create a plurality of digital messages from the incoming analog or digital data stream, where each message contains a portion of the digitized medical sensing data and a header. The aforementioned U.S. Patent Application No. 61/473,591, entitled "Distributed Medical Sensing System and Method," discloses creating messages associating identifying information with medical sensing data in more detail. Further, in some embodiments, the controller 1512 may be operable to modify the medical data received from the medical sensing devices as it is routed to the communication module 1516. For example, in some embodiments, the controller 1512 may compress the data before it is transmitted over the network 1428. In some embodiments, the controller 1512 may also be operable to filter incoming sensing data in some manner.

In embodiments in which the network 1428 is packet-based, the communication module 1516 is operable to packetize medical sensing data routed by (and possibly digitized by) the controller 1512, address the resulting packets, and the send the packets out over the network 1428 via a socket 1518. In the embodiments in which the controller 1512 segments incoming sensing data into messages, the communication module 1512 may encapsulate the messages into TCP/IP packets for transmission over the network 1428. In some embodiments, the PIM 1502 may wirelessly transmit unprocessed medical sensing data to the network 1428 like PIM 1504, and, as such, the communication module 1516 may be a wireless communication module. The PIM 1502 further includes a medical-grade power supply unit (PSU) 1520. The PSU 1520 provides power to the controller 1512, wireless module 1516, and the phased-array transducers disposed on catheter 1408 via the catheter's connection to socket 1510. In some embodiments, the PSU 1520 may be able to dynamically deliver varying amounts of power to socket 1510 based on the type of catheter coupled to socket 1510. For instance, the PSU may include a secondary-stage switching power converter similar to the power converters in the BUB 1401 of FIG. 16.

Although illustrative embodiments have been shown and described, a wide range of modification, change, and substitution is contemplated in the foregoing disclosure and in some instances, some features of the present disclosure may be employed without a corresponding use of the other features. For example, in some embodiments, the medical sensing communication system 100 may be used to process non-cardiovascular diagnostic data such as data from cranial or peripheral arteries, as well as data from non-vascular body portions. Further, the system 100 may be used to collect and process MRI data, or may be utilized in computer assisted surgery (CAS) applications. And, as such, the hub 101 may be configured to communicatively couple medical tools related to non-cardiovascular diagnostic data collection and analysis to a remote processing system. In this regard, the hub 101 may include any number of different and/or additional connector types, links, and internal modules related to any number of medical fields. Further, any number of additional mounting brackets may be coupled to the hub 101 to position it in any number of positions within a medical procedure room or laboratory. Similarly, in some embodiments, the medical sensing communication system 1400 may be used to process non-cardiovascular diagnostic data such data from cranial or peripheral arteries, as well as data from non-vascular body portions. Further, the system 1400 may be used to collect and process MRI data, or may be utilized in computer assisted surgery (CAS) applications. It is understood that such variations may be made in the foregoing without departing from the scope of the present disclosure. Accordingly, it is appropriate that the appended claims be construed broadly and in a manner consistent with the scope of the present disclosure. It is understood that such variations may be made in the foregoing without departing from the scope of the present disclosure. Accordingly, it is appropriate that the appended claims be construed broadly and in a manner consistent with the scope of the present disclosure.

What is claimed is:

1. A patient communication system comprising:
 a first medical sensing device operable to collect first medical data associated with a first modality, the first medical sensing device including a flexible elongate member sized and shaped for insertion into a vessel of a patient body, wherein the first modality is an intravascular modality;
 an analog to digital converter communicatively coupled to the first medical sensing device and operable to digitize the first medical data;
 a network communication module communicatively coupled to the first medical sensing device and a data network, the network communication module operable to transmit the digitized first medical data onto the data network;
 a controller communicatively coupled to the analog to digital converter and the network communication module and operable route the first medical sensing data to the network communication module;
 a power source operable to provide power to the first medical sensing device, the controller, and the network communication module;
 a hub including the analog to digital converter, controller, and network communication module;
 a second medical sensing device operable to collect second medical data associated with a second modality different from the first modality; and
 a patient interface module communicatively coupled to the hub and operable to receive the second medical data from the second medical sensing device and transmit the second medical data to the hub, the patient interface module being further operable to route power from the power source to the second medical sensing device.

2. The patient communication system of claim 1,
 including a further patient interface module communicatively coupled to the first medical sensing device and the hub and operable to receive the first medical data from the first medical sensing device and transmit the first medical data to the hub, the further patient interface module being further operable to route power from the power source to the first medical sensing device.

3. The patient communication system of claim 2, wherein the power source is operable to dynamically provide a first amount of power to the further patient interface module based upon a power requirement of the first medical sensing device and dynamically provide a second amount of power to the patient interface module based upon a power requirement of the second medical sensing device, the first amount of power being different from the second amount of power.

4. The patient communication system of claim 1, wherein the controller is operable to process the first medical data using a first processing application associated with the first modality to produce first processed medical data and is operable to process the second medical data using a second processing application associated with the second modality to produce second processed medical data.

5. The patient communication system of claim 1, wherein the controller is operable to process the first and second medical data using a co-registration processing application to produce co-registered medical data.

6. The patient communication system of claim 1, wherein the power source is operable to dynamically provide an amount of power to the first medical sensing device, the amount of power being based upon power requirements of the first medical sensing device.

7. The patient communication system of claim 1,
 including a graphics controller communicatively coupled to the controller;
 wherein the controller is operable to process the first medical data using a processing application associated with the first modality to produce first processed medical data; and wherein the graphics controller is operable to drive the first processed medical data to a display.

8. The patient communication system of claim 7, wherein the processing application is one of a plurality of processing applications executable by the controller, the plurality of processing applications including processing applications associated with modalities different from the first modality.

9. The patient communication system of claim 1, wherein the first medical sensing device includes at least one of a catheter or a guide wire.

10. The patient communication system of claim 9, wherein the first medical sensing device includes a sensor configured for at least one of intravascular ultrasound (IVUS) imaging, optical coherence tomography (OCT) imaging, a fractional flow reserve (FFR) determination, forward looking IVUS (FLIVUS) imaging, and intravascular photoacoustic (IVPA) imaging.

11. The patient communication system of claim 1, wherein the network communication module is wirelessly communicatively coupled to the first medical sensing device.

12. The patient communication system of claim 1, wherein the network communication module wirelessly communicatively coupled to the data network.

13. The patient communication system of claim 1, wherein at least one of the analog to digital converter, the network communication module, the controller, or the power source are operable to interface with the second medical sensing device associated with the second modality to facilitate a multi-modality medical sensing procedure associated with both the first modality and the second modality.

14. A patient communication system comprising:
 a first medical sensing device operable to collect first medical data associated with a first modality, the first medical sensing device including a flexible elongate member sized and shaped for insertion into a vessel of a patient body, wherein the first modality is an intravascular modality;
 an analog to digital converter communicatively coupled to the first medical sensing device and operable to digitize the first medical data;
 a network communication module communicatively coupled to the first medical sensing device and a data network, the network communication module operable to transmit the digitized first medical data onto the data network;
 a controller communicatively coupled to the analog to digital converter and the network communication module and operable route the first medical sensing data to the network communication module;
 a power source operable to provide power to the first medical sensing device, the controller, and the network communication module;
 a hub including the controller and the network communication module;
 a first patient interface module (PIM) communicatively coupled to the hub and the first medical sensing device, the first PIM including the analog to digital converter;
 a second medical sensing device operable to collect second medical data associated with a second modality different from the first modality; and a second PIM communicatively coupled to the hub and operable to receive the second medical data from the second medical sensing device and transmit the second medical data to the hub, the second PIM further operable to route power from the power source to the second medical sensing device.

15. The patient communication system of claim 14, wherein the first PIM is operable to receive the first medical data from the first medical sensing device and transmit the first medical data to the hub, the first PIM being further operable to route power from the power source to the first medical sensing device.

16. The patient communication system of claim 15, wherein the power source is operable to dynamically provide a first amount of power to the first PIM based upon a power requirement of the first medical sensing device and dynamically provide a second amount of power to the second PIM based upon a power requirement of the second medical sensing device, the first amount of power being different from the second amount of power.

17. The patient communication system of claim 14, wherein the controller is operable to process the first medical data using a first processing application associated with the first modality to produce first processed medical data and is operable to process the second medical data using a second processing application associated with the second modality to produce second processed medical data.

18. The patient communication system of claim 14, wherein the controller is operable to process the first and second medical data using a co-registration processing application to produce co-registered medical data.

19. The patient communication system of claim 14, wherein the power source is operable to dynamically provide an amount of power to the first medical sensing device, the amount of power being based upon power requirements of the first medical sensing device.

20. The patient communication system of claim 14, including a graphics controller communicatively coupled to the controller;
wherein the controller is operable to process the first medical data using a processing application associated with the first modality to produce first processed medical data; and wherein the graphics controller is operable to drive the first processed medical data to a display.

21. The patient communication system of claim 20, wherein the processing application is one of a plurality of processing applications executable by the controller, the plurality of processing applications including processing applications associated with modalities different from the first modality.

22. The patient communication system of claim 14, wherein the first medical sensing device includes at least one of a catheter or a guide wire.

23. The patient communication system of claim 22, wherein the first medical sensing device includes a sensor configured for at least one of intravascular ultrasound (IVUS) imaging, optical coherence tomography (OCT) imaging, a fractional flow reserve (FFR) determination, forward looking IVUS (FLIVUS) imaging, and intravascular photoacoustic (IVPA) imaging.

24. The patient communication system of claim 14, wherein the network communication module is wirelessly communicatively coupled to the first medical sensing device.

25. The patient communication system of claim 14, wherein the network communication module wirelessly communicatively coupled to the data network.

26. The patient communication system of claim 14, wherein at least one of the analog to digital converter, the network communication module, the controller, or the power source are operable to interface with the second medical sensing device associated with the second modality to facilitate a multi-modality medical sensing procedure associated with both the first modality and the second modality.

* * * * *